US006596314B2

(12) United States Patent
Wong et al.

(10) Patent No.: US 6,596,314 B2
(45) Date of Patent: Jul. 22, 2003

(54) CONTROLLED RELEASE LIQUID ACTIVE AGENT FORMULATION DOSAGE FORMS

(75) Inventors: Patrick S. -L. Wong, Burlingame, CA (US); David E. Edgren, Los Altos, CA (US); Liang C. Dong, Sunnyvale, CA (US); Crystal Pollock-Dove, Mountain View, CA (US)

(73) Assignee: Alza Corporation, Palo Alto, CA (US)

( * ) Notice: Subject to any disclaimer, the term of this patent is extended or adjusted under 35 U.S.C. 154(b) by 0 days.

(21) Appl. No.: 10/022,300

(22) Filed: Dec. 14, 2001

(65) Prior Publication Data

US 2002/0086055 A1 Jul. 4, 2002

Related U.S. Application Data

(63) Continuation of application No. 09/470,088, filed on Dec. 22, 1999, now Pat. No. 6,342,249.
(60) Provisional application No. 60/113,559, filed on Dec. 23, 1998.

(51) Int. Cl.$^7$ .............................. A61K 9/22; A61K 9/24
(52) U.S. Cl. ........................ 424/473; 424/468; 424/472
(58) Field of Search ................................ 424/473, 468, 424/489, 472, 469, 470

(56) References Cited

U.S. PATENT DOCUMENTS

| 2,707,154 A | 4/1955 | Lehmann, et al. |
| 2,799,241 A | 7/1957 | Wurster, et al. |
| 2,805,977 A | 10/1957 | Robinson, et al. |

(List continued on next page.)

FOREIGN PATENT DOCUMENTS

| EP | 0 163 178 | 5/1985 |
| EP | 0 448 091 A2 | 9/1991 |
| EP | 0 985 411 A1 | 3/2000 |
| GB | 2 155 889 A | 10/1985 |
| WO | WO 98/38987 | 9/1998 |

OTHER PUBLICATIONS

Berge, et al ; Pharmaceutical Salts ; Journal of Pharmaceutical Sciences ; vol. 66, No. 1 ; pp. 1–19 (Jan. 1977).
Considine, P.E, Douglas M. ; Van Nostrand Reinhold Encyclopedia of Chemistry 4th Edition ; pp. 644–645 (1986).
Hixon, et al ; Sizing Materials By Crushing and Grinding ; Chemical Engineering ; pp. 94–103 (Nov. 1990).
Parrott, Eugene L.; Milling of Pharmaceutical Solids ; Journal of Pharmaceutical Sciences ; vol. 63, No. 6 ; pp. 813–829 (Jun. 1974).
Perry ; Screening ; Chemical Engineering Handbook 6th Edition ; pp. 21–13 to 21–19 ; (1984).
Ripple, Edward G. Ph.D.; Powders ; Pharmaceutical Sciences Remington 17th Edition ; pp. 1585–1594 (1985).
Rouse, B.P. Jr.; Cellulose Esters, Organic ; Encyclopedia of Polymer Sciecne & Technology vol. 3, pp. 325–354 (1964).
Sheth, et al. ; Use of Powdered Solution To Improve The Disolution Rate of Poluthiazide Tablets ; Drug Development and Industrial Pharmacy ; 16(5) ; pp. 769–777 (1990).
Wurster, Dale E. ; Air–Suspension Technique of Coating Drug Particles A Preliminary Report ; Journal of Americal Pharmaceutical Association Scientific Edition ; vol. 48 ; pp. 451–459 (Aug. 1959).
Wurster, Dale E. ; Preparation of Compressed Tablet Granulations by the Air–Suspension Technique II ; Journal of Americal Pharmaceutical Association Scientific Edition; vol. 49, No. 2 ; pp. 82–84 (Feb. 1960).
Pharmaceuticals Sciences by Remington 17th Edition, pp. 403–405, (1985).

*Primary Examiner*—James M. Spear
(74) *Attorney, Agent, or Firm*—Samuel E. Webb

(57) ABSTRACT

Controlled release of liquid, active agent formulations is provided by dispersing porous particles containing the liquid active agent formulation in osmotic, push-layer dosage forms. The dosage forms may provide for continuous or pulsatile delivery of active agents.

5 Claims, 8 Drawing Sheets

U.S. PATENT DOCUMENTS

| | | | |
|---|---|---|---|
| 3,133,132 A | 5/1964 | Loeb, et al. | |
| 3,173,876 A | 3/1965 | Zorbrist, et al. | |
| 3,276,586 A | 10/1966 | Rosaen, et al. | |
| 3,541,005 A | 11/1970 | Strathmann, et al. | |
| 3,541,006 A | 11/1970 | Bixler, et al. | |
| 3,546,142 A | 12/1970 | Michaels, et al. | |
| 3,573,936 A | 4/1971 | Karchmar, et al. | |
| 3,637,772 A | 1/1972 | Klaui, et al. | |
| 3,845,770 A | 11/1974 | Theeuwes, et al. | |
| 3,865,108 A | 2/1975 | Hartop | |
| 3,916,899 A | 11/1975 | Theeuwes, et al. | |
| 4,002,173 A | 1/1977 | Manning et al. | |
| 4,038,434 A | 7/1977 | Young | |
| 4,063,064 A | 12/1977 | Saunders et al. | |
| 4,077,407 A | 3/1978 | Theeuwes et al. | |
| 4,088,864 A | 5/1978 | Theeuwes et al. | |
| 4,160,020 A | 7/1979 | Ayer et al. | |
| 4,182,330 A | 1/1980 | Michaels | 128/260 |
| 4,186,465 A | 2/1980 | Manning | 24/201 |
| 4,207,893 A | 6/1980 | Michaels | 604/892.1 |
| 4,259,323 A | 3/1981 | Ranucci | 424/153 |
| 4,559,237 A | 12/1985 | Meier et al. | 427/53.1 |
| 4,892,778 A | 1/1990 | Theeuwes et al. | 427/53.1 |
| 4,915,949 A | 4/1990 | Wong et al. | 424/438 |
| 4,931,285 A | 6/1990 | Edgren et al. | 424/473 |
| 4,940,465 A | 7/1990 | Theeuwes et al. | 604/892.1 |
| 5,006,346 A | 4/1991 | Edgren et al. | 424/473 |
| 5,024,842 A | 6/1991 | Edgren et al. | 424/473 |
| 5,110,597 A | 5/1992 | Wong et al. | 424/438 |
| 5,112,817 A | 5/1992 | Fukazawa et al. | 514/183 |
| 5,126,142 A | 6/1992 | Ayer et al. | 424/439 |
| 5,160,743 A | 11/1992 | Edgren et al. | 424/473 |
| 5,190,765 A | 3/1993 | Jao et al. | 424/473 |
| 5,223,265 A | 6/1993 | Wong | 424/473 |
| 5,252,338 A | 10/1993 | Jao et al. | 424/473 |
| 5,312,390 A | 5/1994 | Wong | 604/892.1 |
| 5,417,682 A | 5/1995 | Wong et al. | 604/892.1 |
| 5,443,459 A | 8/1995 | Wong et al. | 604/892.1 |
| 5,486,365 A | 1/1996 | Takado et al. | 424/602 |
| 5,498,255 A | 3/1996 | Wong | 604/892.1 |
| 5,531,736 A | 7/1996 | Wong et al. | 604/892.1 |
| 5,534,263 A | 7/1996 | Wong et al. | 424/473 |
| 5,620,705 A | 4/1997 | Dong et al. | 424/473 |
| 5,633,011 A | 5/1997 | Dong et al. | 424/451 |
| 5,643,909 A | 7/1997 | Pfister et al. | 514/253 |
| 5,660,861 A | 8/1997 | Jao et al. | 424/465 |
| 5,800,422 A | 9/1998 | Dong et al. | 604/892.1 |
| 5,800,834 A | 9/1998 | Spireas et al. | 424/451 |
| 5,824,638 A | 10/1998 | Burnside et al. | 514/3 |
| 5,955,086 A | 9/1999 | DeLuca et al. | 424/195.1 |
| 6,342,249 B1 * | 1/2002 | Wong et al. | 424/473 |

* cited by examiner

CONTROLLED RELEASE LIQUID ACTIVE AGENT FORMULATION DOSAGE FORMS

This application claims the priority of application Ser. No. 09/470,088, U.S. Pat. No. 6,342,249, filed Dec. 22, 1999, which claims the priority of provisional application No. 60/113,559, filed Dec. 23, 1998, which are incorporated herein by reference.

FIELD OF THE INVENTION

This invention pertains to the controlled delivery of pharmaceutical agents and dosage forms therefor. In particular, the invention is directed to improved methods, dosage forms and devices for the controlled delivery of liquid active agent formulations to an environment of use.

BACKGROUND OF THE INVENTION

Administration of liquid, active agent formulations is often preferred over solid active agent formulations in order to facilitate absorption of the active agent and obtain a beneficial effect for the intended use in the shortest possible time after the formulation is exposed to the environment of use. Examples of prior art devices to deliver liquid, active agent formulations are soft gelatin capsules that contain a liquid active agent formulation or liquid formulations of the active agent that are bottled and dispensed in measured dosage amounts by the spoonful, or the like. Those systems are not generally amenable to controlled delivery of the active agent over time. While it is desired to have the active agent exhibit its effect as soon as it is released to the environment of use, it also often is desirable to have controlled release of the active agent to the environment of use over time. Such controlled release may be sustained delivery over time, such as zero order, or patterned delivery, such as pulsatile for example. Prior art systems have not generally been suitable for such delivery.

Various devices and methods have been described for the continuous delivery of active agents over time. Typically, such prior art systems have been used to deliver active agents initially in the dry state prior to administration. For example, U.S. Pat. Nos. 4,892,778 and 4,940,465, which are incorporated herein by reference, describe dispensers for delivering a beneficial agent to an environment of use that include a semipermeable wall defining a compartment containing a layer of expandable material that pushes a drug layer out of the compartment formed by the wall. The exit orifice in the device is substantially the same diameter as the inner diameter of the compartment formed by the wall.

U.S. Pat. No. 4,915,949, which is incorporated herein by reference, describes a dispenser for delivering a beneficial agent to an environment of use that includes a semipermeable wall containing a layer of expandable material that pushes a drug layer out of the compartment formed by the wall. The drug layer contains discrete tiny pills dispersed in a carrier. The exit orifice in the device is substantially the same diameter as the inner diameter of the compartment formed by the wall.

U.S. Pat. No. 5,126,142, which is incorporated herein by reference, describes a device for delivering an ionophore to livestock that includes a semipermeable housing in which a composition containing the ionophore and a carrier and an expandable hydrophilic layer is located, along with an additional element that imparts sufficient density to the device to retain it in the rumen-reticular sac of a ruminant animal. The ionophore and carrier are present in a dry state during storage and the composition changes to a dispensable, fluid-like state when it is in contact with the fluid environment of use. A number of different exit arrangements are described, including a plurality of holes in the end of the device and a single exit of varying diameter to control the amount of drug released per unit time due to diffusion and osmotic pumping.

It is often preferable that a large orifice, from about 50%–100% of the inner diameter of the drug compartment, be provided in the dispensing device containing the active agent and a bioerodible or degradable active agent carrier. When exposed to the environment of use, drug is released from the drug layer by erosion and diffusion. In those cases where the drug is present in the solid state, the realization of the beneficial effect is delayed until the drug is dissolved in the fluids of the environment of use and absorbed by the tissues or mucosal environment of the gastrointestinal tract. Such delay often is not tolerable. Also, for drugs that are poorly soluble in gastric or intestinal fluids, the delay may be further exacerbated.

Devices in which the drug composition initially is dry but in the environment of use is delivered as a slurry, suspension or solution from a small exit orifice by the action of an expandable layer are described in U.S. Pat. Nos. 5,660,861; 5,633,011; 5,190,765; 5,252,338; 5,620,705; 4,931,285; 5,006,346; 5,024,842; and 5,160,743. Typical devices include an expandable push layer and a drug layer surrounded by a semipermeable membrane.

When the active agent is insoluble or poorly soluble, prior art systems may not provide rapid delivery of active agent or concentration gradients at the site of absorption that facilitate absorption through the gastrointestinal tract. Various approaches have been put forth to address such problems, including the use of water-soluble salts, self-emulsifying compositions, polymorphic forms, powdered solutions, molecular complexes, micronization, eutectics, and solid solutions. An example of the use of a powdered solution is described by Sheth, et al., in "Use of Powdered Solutions to Improve the Dissolution Rate of Polythiazide Tablets," Drug Development and Industrial Pharmacy, 16(5), 769–777 (1990). References to certain of the other approaches are cited therein. Additional examples of powdered solutions are described in U.S. Pat. No. 5,800,834. The patent describes methodology for calculating the amount of liquid that may be optimally sorbed into materials to prevent the drug solution from being exuded from the granular composition during compression.

U.S. Pat. No. 5,486,365, which is incorporated herein by reference, describes a spheronized material formed from a scale-like calcium hydrogen phosphate particulate material having a high specific surface area, good compressibility and low friability. That patent indicates that the material has the characteristic of high liquid absorption. However, the patent does not suggest that the material may be used as a carrier for delivery of a liquid medicament formulation to the environment of use. Instead, the patent describes the formation of a dried formulation, such as formed by spray drying. The patent describes the use of a suspension containing medicines and binders during the spray-drying granulation process to form a spherical particle containing the medicine. As an example, ascorbic acid in an amount equivalent to 10% of the scale-like calcium hydrogen phosphate was dissolved into a slurry of 20 weight percent of calcium hydrogen phosphate in water, and the resulting slurry was spray dried to form dried, spherical calcium hydrogen phosphate containing ascorbic acid. That material was then tableted under loads of 500–2000 $kg/cm^2$.

SUMMARY OF THE INVENTION

It has been surprisingly discovered that certain absorbent materials having prescribed physical characteristics, as exemplified by, for example, particular porous calcium hydrogen phosphate powders described in U.S. Pat. No. 5,486,365, sold under the trademark FujiCalin®, and magnesium aluminometasilicate powders, sold under the trademark Neusilin™ (Fuji Chemical Industries (U.S.A.) Inc., Robbinsville, N.J.), may be used to prepare dosage forms in which liquid, active agent formulations may be sorbed into the interior pores of the aforementioned materials in significant amounts and delivered to the site of administration in the liquid state. It has further been surprisingly discovered that such types of porous particles with liquid, active agent formulations sorbed into the particles may be fabricated into controlled release dosage forms without exuding the liquid, active agent formulation out of the particles during the manufacturing process. That discovery has permitted the fabrication of controlled release dosage forms that provided for the delivery of the active agent to the delivery site in the liquid state, thus providing minimal delay in the onset of the desired beneficial effect of the active agent, since the active agent does not have to be initially dissolved or dispersed in the form of microparticles at the site of action. Furthermore, such dosage forms may permit large concentration gradients of active agent in solution, and optional delivery of absorption enhancers, at the absorption site to facilitate absorption of the active agent. Microcrystalline cellulose, porous sodium carboxymethyl cellulose crosslinked sold as Ac-Di-Sol (FMC Corporation), porous soy bean hull fiber sold as Fl-1 Soy Fiber (Fibred Group), and silicon dioxide having high surface area and good absorption properties may also be used in the dosage forms described herein. However, the calcium hydrogen phosphate and magnesium aluminometasilicate particles as described herein are presently preferred.

Accordingly, in one aspect, the invention comprises a dosage form for an active agent comprising a wall defining a cavity, the wall having an exit orifice formed or formable therein and at least a portion of the wall being semipermeable; an expandable layer located within the cavity remote from the exit orifice and in fluid communication with the semipermeable portion of the wall; a drug layer located within the cavity adjacent the exit orifice and in direct or indirect contacting relationship with the expandable layer; the drug layer comprising a liquid, active agent formulation absorbed in porous particles, the porous particles being adapted to resist compaction forces sufficient to form a compacted drug layer without significant exudation of the liquid, active agent formulation. Optionally, a flow-promoting layer may be interposed between the inner surface of the wall and at least the external surface of the drug layer located within the cavity. Also, a placebo layer to delay onset of delivery of the active agent optionally may be placed between the drug layer and the exit orifice.

In another aspect, the invention comprises a dosage form for an active agent comprising a wall defining a cavity, the wall having an exit orifice formed or formable therein and at least a portion of the wall being semipermeable; an expandable layer located within the cavity remote from the exit orifice and in fluid communication with the semipermeable portion of the wall; a drug layer located within the cavity adjacent the exit orifice and in direct or indirect contacting relationship with the expandable layer; the drug layer comprising a liquid, active agent formulation absorbed in porous particles, the porous particles, having a mean particle size of 50–150 microns, being formed by spray drying a scale-like calcium hydrogen phosphate with a specific surface area of 20 m$^2$/g to 60 m$^2$/g, an apparent specific volume of 1.5 ml/g or more, an oil absorption capacity of 0.7 ml/g or more, a primary particle size of 0.1$\mu$ to 5$\mu$, and an average particle size of 2$\mu$ to 10$\mu$ among secondary particles that are aggregates of the primary particles, the scale-like calcium hydrogen phosphate being represented by the following general formula:

$$CaHPO_4 \cdot mH_2O$$

wherein m satisfies the relationship $0 \leq m \leq 2.0$.

In yet another aspect, the invention comprises a dosage form for an active agent comprising a wall defining a cavity, the wall having an exit orifice formed or formable therein and at least a portion of the wall being semipermeable; an expandable layer located within the cavity remote from the exit orifice and in fluid communication with the semipermeable portion of the wall; a drug layer located within the cavity adjacent the exit orifice and in direct or indirect contacting relationship with the expandable layer; the drug layer comprising a liquid, active agent formulation absorbed in porous particles, the porous particles being calcium hydrogen phosphate having a specific volume of at least 1.5 ml/g, a BET specific surface area of at least 20 m$^2$/g, and a water absorption capacity of at least 0.7 ml/g. Preferably, the particles have a bulk density of 0.4–0.6 g/ml, a BET surface area of 30–50 m$^2$/g, a specific volume of greater than 2 ml/g, and a mean pore size of at least 50 Angstroms.

In another aspect, the invention comprises a dosage form for an active agent comprising a wall defining a cavity, the wall having an exit orifice formed or formable therein and at least a portion of the wall being semipermeable; an expandable layer located within the cavity remote from the exit orifice and in fluid communication with the semipermeable portion of the wall; a drug layer located within the cavity adjacent the exit orifice and in direct or indirect contacting relationship with the expandable layer; the drug layer comprising a liquid, active agent formulation absorbed in porous particles, the porous particles being calcium hydrogen phosphate having a specific volume of at least 1.5 ml/g, a BET specific area of at least 20 m$^2$/g, and a water absorption capacity of at least 0.7 ml/g, the particles having a size distribution of 100% less than 40 mesh, 50%–100% less than 100 mesh and 10%–60% less than 200 mesh. Preferably, 100% is less than 40 mesh, 60%–90% is less than 100 mesh and 20%–60% is less than 200 mesh.

In yet another aspect, the invention comprises a dosage form for an active agent comprising a wall defining a cavity, the wall having an exit orifice formed or formable therein and at least a portion of the wall being semipermeable; an expandable layer located within the cavity remote from the exit orifice and in fluid communication with the semipermeable portion of the wall; a drug layer located within the cavity adjacent the exit orifice and in direct or indirect contacting relationship with the expandable layer; the drug layer comprising a liquid, active agent formulation absorbed in porous particles, the porous particles being calcium hydrogen phosphate having a bulk specific volume of 1.5 ml/g–5 ml/g, a BET specific area of 20 m$^2$/g-60 m$^2$/g, a water absorption capacity of at least 0.7 ml/g, and a mean particle size of at least 70 micrometers.

In still another aspect, the invention comprises a dosage form for an active agent comprising a wall defining a cavity, the wall having an exit orifice formed or formable therein and at least a portion of the wall being semipermeable; an expandable layer located within the cavity remote from the exit orifice and in fluid communication with the semipermeable portion of the wall; a drug layer located within the cavity adjacent the exit orifice and in direct or indirect contacting relationship with the expandable layer; the drug layer comprising a liquid, active agent formulation absorbed in porous particles, the porous particles being adapted to resist compaction forces sufficient to form a compacted drug layer without significant exudation of the liquid, active agent formulation, the dosage form optionally comprising a placebo (inert) layer between the exit orifice and the drug layer. Optionally, a flow-promoting layer may be interposed between the inner surface of the wall and at least the external surface of the drug layer located within the cavity.

In yet another aspect, the invention comprises a method of facilitating the release of an active agent from a dosage form comprising sorbing a liquid formulation of the active agent into a plurality of porous particles, the particles, having a mean particle size of 50–150 microns, being formed by spray drying a scale-like calcium hydrogen phosphate with a specific surface area of 20 m²/g to 60 m²/g, an apparent specific volume of 1.5 ml/g or more, an oil absorption capacity of 0.7 ml/g or more, a primary particle size of $0.1\mu$ to $5\mu$, and an average particle size of $2\mu$ to $10\mu$ among secondary particles that are aggregates of the primary particles, the scale-like calcium hydrogen phosphate being represented by the following general formula:

$$CaHPO_4.mH_2O$$

wherein m satisfies the relationship $0 \leq m \leq 2.0$, and dispersing the particles throughout a bioerodible carrier.

In another aspect, the invention comprises a composition comprising a liquid formulation of the active agent sorbed into a plurality of porous particles, the particles, having a mean particle size of 50–150 microns, being formed by spray drying a scale-like calcium hydrogen phosphate with a specific surface area of 20 m²/g to 60 m²/g, an apparent specific volume of 1.5 ml/g or more, an oil absorption capacity of 0.7 ml/g or more, a primary particle size of $0.1\mu$ to $5\mu$, and an average particle size of $2\mu$ to $10\mu$ among secondary particles that are aggregates of the primary particles, the scale-like calcium hydrogen phosphate being represented by the following general formula:

$$CaHPO_4.mH_2O$$

wherein m satisfies the relationship $0 \leq m \leq 2.0$, and dispersed throughout a bioerodible carrier, the particles being released in the environment of use over a prolonged period of time.

In yet another aspect, the invention comprises a dosage form for an active agent comprising a wall defining a cavity, the wall having an exit orifice formed or formable therein and at least a portion of the wall being semipermeable; an expandable layer located within the cavity remote from the exit orifice and in fluid communication with the semipermeable portion of the wall; a drug layer located within the cavity adjacent the exit orifice and in direct or indirect contacting relationship with the expandable layer; the drug layer comprising a liquid, active agent formulation absorbed in porous particles, the porous particles being magnesium aluminometasilicate.

In still another aspect, the invention comprises a dosage form for an active agent comprising a wall defining a cavity, the wall having an exit orifice formed or formable therein and at least a portion of the wall being semipermeable; an expandable layer located within the cavity remote from the exit orifice and in fluid communication with the semipermeable portion of the wall; a drug layer located within the cavity adjacent the exit orifice and in direct or indirect contacting relationship with the expandable layer; the drug layer comprising a liquid, active agent formulation absorbed in porous particles, the porous particles being magnesium aluminometasilicate represented by the general formula $$Al_2O_3.MgO.2SiO_2.nH_2O$$

wherein n satisfies the relationship $0 \leq n \leq 10$.

In another aspect, the invention comprises a dosage form for an active agent comprising a wall defining a cavity, the wall having an exit orifice formed or formable therein and at least a portion of the wall being semipermeable; an expandable layer located within the cavity remote from the exit orifice and in fluid communication with the semipermeable portion of the wall; a drug layer located within the cavity adjacent the exit orifice and in direct or indirect contacting relationship with the expandable layer; the drug layer comprising a liquid, active agent formulation absorbed in porous particles, the porous particles being magnesium aluminometasilicate represented by the general formula $$Al_2O_3.MgO.2SiO_2.nH_2O$$

wherein n satisfies the relationship $0 \leq n \leq 10$ and having a specific surface area of about 100–300 m²/g, an oil absorption capacity of about 1.3–3.4 ml/g, a mean particle size of about 1–2 microns, an angle of repose about 25°–45°, a specific gravity of about 2 g/ml and a specific volume of about 2.1–12 ml/g.

The dosage forms of the invention may be fabricated with inert spacers between one or more drug layers to provide for pulsatile drug delivery or with a plurality of drug layers, each having a different active agent. Different active agents may be included within a single drug layer.

Generally, 5% and up to 70%, more often 20–70%, preferably 30–60%, and more preferably 40–60%, by weight of the liquid, active agent formulation may be loaded into the porous particles. Up to about 50% by weight of liquid active agent formulation may be loaded into the porous crystalline materials, such as calcium hydrogen phosphate particles, but more typically 30–40 weight percent. Higher loading is possible with amorphous porous carriers such as magnesium aluminometasilicates, which may contain up to 60–70% liquid, active agent formulation, more usually up to 60%. A small amount of a binder, e.g. up to 5–10% by weight, may be added to form the active agent layer with calcium hydrogen phosphate particles, as well as a tableting lubricant. For amorphous materials, usually less or no binder and lubricant are used. Blends of the various absorptive materials described herein may be used, such as for example, blends of crystalline material such as calcium hydrogen phosphate with the amorphous material such as magnesium aluminosilicate.

DETAILED DESCRIPTION OF THE INVENTION

Figure 1:
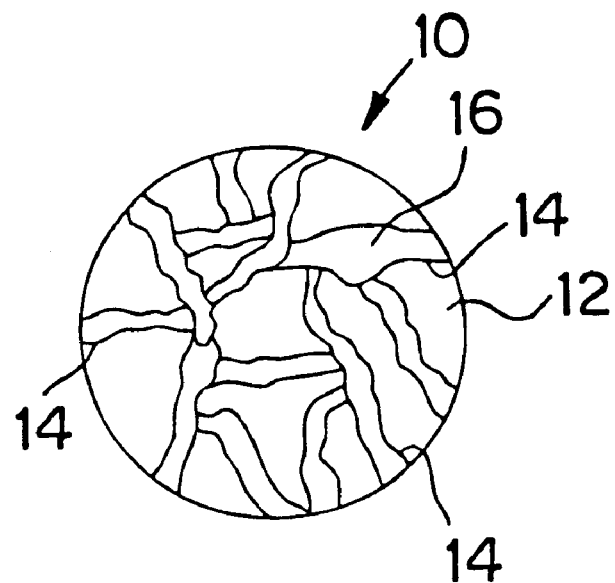
FIG. 1 illustrates a porous particle containing a liquid, active agent formulation utilized in the present invention.

The present invention is best understood by reference to the following definitions, the drawings and exemplary disclosure provided herein.

Definitions:

By "active agent", "drug", or "compound", which are used interchangeably herein, is meant an agent, drug, compound, composition of matter or mixture thereof which provides some physiological, psychological, biological, or pharmacological, and often beneficial, effect when in the environment of use.

By "uniform rate of release" or "uniform release rate" is meant a rate of release of the active agent from a dosage form that does not vary positively or negatively by more than 30% from the mean rate of release of the active agent over a prolonged period of time, as determined in a USP Type 7 Interval Release Apparatus. Preferred uniform rates of release will vary by not more than 25% (positively or negatively) from the mean rate of release determined over a prolonged period of time.

By "prolonged period of time" or "prolonged period" is meant a continuous period of time of 4 hours or more, more typically 6 hours or more.

By "dosage form" is meant a pharmaceutical composition or device comprising an active pharmaceutical agent, the composition or device optionally containing inactive ingredients, such as pharmaceutically-acceptable carriers, excipients, suspension agents, surfactants, disintegrants, binders, diluents, lubricants, stabilizers, antioxidants, osmotic agents, colorants, plasticizers, and the like, that are used to manufacture and deliver active pharmaceutical agents.

By "pharmaceutically-acceptable acid addition salt" or "pharmaceutically-acceptable salt", which are used interchangeably herein, are meant those salts in which the anion does not contribute significantly to the toxicity or pharmacological activity of the salt, and, as such, they are the pharmacological equivalents of the bases of the compounds to which they refer. Examples of pharmaceutically acceptable acids that are useful for the purposes of salt formation include but are not limited to hydrochloric, hydrobromic, hydroiodic, citric, acetic, benzoic, mandelic, fumaric, succinic, phosphoric, nitric, mucic, isethionic, palmitic, and others.

By "sustained release" is meant continuous release of active agent to an environment of use over a prolonged period.

By "pulsatile release" is meant release of an active agent to an environment of use for one or more discrete periods of time preceded or followed by (i) at least one discrete period of time in which the active agent is not released, or (ii) at least one period of time in which another, different active agent is released. Pulsatile release is meant to include delayed release of active agent following administration of the dosage form and release in which one or more pulses of active agent are released over a period of time.

By "steady state" is meant the condition in which the amount of drug present in the blood plasma of a subject does not vary significantly over a prolonged period of time.

By "release rate assay" is meant a standardized assay for the determination of a compound using a USP Type 7 interval release apparatus substantially in accordance with the description of the assay contained herein. It is understood that reagents of equivalent grade may be substituted in the assay in accordance with generally-accepted procedures. Also, different fluids such as artificial gastric fluid or artificial intestinal fluid may be used to evaluate release characteristics in environments characterized by different pH values.

By "liquid, active agent formulation" is meant that the active agent is present in a composition that is miscible with or dispersible in the fluids of the environment of use, or is able to flow or diffuse from the pores of the particles into the environment of use. The formulation may be neat, liquid active agent, or a solution, suspension, slurry, emulsion, self-emulsifying composition, colloidal dispersion or other flowable composition in which the active agent is present.

The active agent may be accompanied by a suspension agent, antioxidant, emulsion former, protecting agent, permeation enhancer and the like. The amount of an active agent in a dosage form generally is about 0.05 ng to 5 g or more, with individual dosage forms comprising, for example, 25 ng, 1 mg, 5 mg, 10 mg, 25 mg, 100 mg, 250 mg, 500 mg, 750 mg, 1.0 g, 1.2 g, and the like, of active agent. The system typically can be administered once, twice or thrice daily for pharmaceutical applications, or more or less as required by the particular application. In agricultural applications, systems typically will be applied at longer intervals, such as weekly, monthly, seasonally or the like.

One of the most suitable devices for the controlled release of liquid active agent formulations in accordance with this invention is that having a semipermeable wall defining a compartment, an expandable push layer and a drug layer in the compartment, and an exit orifice formed in the dosage form to permit the drug layer to be dispensed. Within the drug layer is a carrier in which is dispersed a plurality of porous particles in which the liquid, active agent has been sorbed. As the push layer expands, the carrier comprising the drug layer will be forced from the dosage form substantially in the dry state where it will erode and release the porous particles containing the liquid, active agent formulation. After release, the liquid active agent formulation will be immediately available the environment of use in the liquid state, and the porous particles will themselves disintegrate or erode and further release the active agent formulation.

When manufacturing such dosage forms, a common practice is to fabricate a compressed tablet comprising the drug layer and the push layer. Typically, the drug layer composition, conveniently in granulated or powdered form, is compressed in a die cavity of a vertical tabletting press. Then the push layer composition, also conveniently in granular or powdered form, is placed in the die cavity above the drug layer and compressed as well to form a bilayer tablet. During the compression or compacting step of the drug layer, the porous particles should be sufficiently resistant to the compressive forces so as not to be crushed or pulverized to any significant extent and prematurely release the liquid, active agent formulation from the porous particles.

Materials useful for sorbing the liquid, active agent formulations are porous particulates that are characterized by high compressibility or tensile strength to withstand compacting forces applied during compacting steps and minimize exudation of liquid, active agent formulation from the pores; particle flow characteristics that allow for the porous particles to be directly compacted without the use of a binder or with minimal use of a binder; low friability so as to preclude or minimize exudation of the liquid and facilitate tablet cohesion, active agent formulation from the particles during compacting steps; and high porosity so as to absorb an adequate of amount of a liquid, active agent formulation to provide an effective amount of active agent in a dosage form. The particles should be adapted to absorb an amount of liquid, active agent formulation such that a therapeutically effective amount of the active agent may be delivered in a unitary dosage form that is of a size that can be conveniently swallowed by a subject and, preferably provided in four or fewer tablets or capsules for ingestion at the same time. The porosity of the particles may be such that at least 5% and up to 70%, more often 20–70%, preferably 30–60%, and more preferably 40–60%, by weight of the liquid, active agent formulation, based on weight of the particles may be sorbed into the pores of the particles, while the particles exhibit sufficient strength at such degree of active agent loading so as not to significantly be crushed or pulverized by compacting forces to which the particles will be subjected during manufacturing operations. More typically, the liquid, active agent formulation may comprise 30–40% of the weight of the porous particles when the particles are crystalline, such as calcium hydrogen phosphate, but that percentage may be greater, e.g., up to 60–70% or more when more amorphous materials, such as magnesium aluminometasilicates, are used. Blends of crystalline and amorphous material may be utilized. At high loadings, it may be advantageous to use blends of calcium hydrogen phosphate particles and amorphous magnesium aluminometasilicate powders.

Preferred materials are those having a strength to resist compression forces of greater than 1500 kg/cm$^2$ without substantial exudation of the liquid, active agent formulation, and most preferably without the tablet hardness plateauing.

A particularly suitable porous particle is exemplified by the particular form of calcium hydrogen phosphate described in U.S. Pat. No. 5,486,365, which is incorporated herein by reference. As described therein, calcium hydrogen phosphate is prepared by a process yielding a scale-like calcium hydrogen phosphate that can be represented by the formula $CaHPO_4 \cdot mH_2O$ wherein m satisfies the expression $0 \leq m \leq 0.5$. Useful calcium hydrogen phosphate materials may include those of the formula $CaHPO_4 \cdot mH_2O$ wherein m satisfies the expression $0 \leq m \leq 2.0$. The scale-like calcium hydrogen phosphate produced has characteristic physical properties that make it particularly suitable for use in the present invention. The scale-like material provides high specific surface area, high specific volume, high capacity for water and oil absorption, and the ability to readily form into spheres upon spray drying. The spherical particulates have excellent flow properties and permit direct compaction into tablets without binders and without significant crushing or pulverizing of the particles during the compaction step.

The scale-like calcium hydrogen phosphate particles generally have a BET specific surface area of at least 20 m$^2$/g, typically 20 m$^2$/g-60 m$^2$/g, a specific volume of at least 1.5 ml/g, typically 2–5 ml/g or more, and an oil and water absorption capacity of at least 0.7 ml/g, typically 0.8–1.5 ml/g. When formed into spheres the spherical particulates may have a mean particle size a mean particle size of 50 microns or greater, usually about 50–150 microns, and often about 60–120 microns. The particle size distribution may be 100% through 40 mesh, 50%–100% through 100 mesh, and 20%–60% through 200 mesh. The bulk density may be from about 0.4 g/ml-0.6 g/ml.

A most preferred form of calcium hydrogen phosphate is that sold under the trademark FujiCalin® by Fuji Chemical Industries (U.S.A.) Inc., Robbinsville, N.J., in types SG and S. Typical parameters for that material include a mean particle size of 500–150 microns, a mean pore size on the order of 70 Angstroms, a specific volume of about 2 ml/g, a BET specific surface area of about 30–40 m$^2$/g, and an oil and water absorption capacity of about 0.7 ml/g. Type SG typically will have a mean particle size of about 113 microns, and a particle size distribution of 100% through 40 mesh, 60% through 100 mesh and 20 through 200 mesh. Type S typically will have a mean particle size of about 68 microns, and a particle size distribution of 100% through 40 mesh, 90% through 100 mesh and 60% through 200 mesh. Mixtures of the two types may be conveniently employed to provide particulates having physical characteristics that are suitable for various applications, as may be determined by those skilled in the art of pharmaceutical formulation, tableting and manufacturing.

The calcium hydrogen phosphate has low friability, demonstrating a tensile strength of up to about 130 kg/cm$^2$ when subjected to compressive forces of up to 3000 kg/cm$^2$. The hardness of the tableted material tends not to plateau at compression forces to that limit, while materials such as microcrystalline cellulose (Avicel PH 301), lactose, DI-TAB and Kyowa GS tend to plateau at or about 700–1500 Kg/cm$^2$. The angle of repose for the preferred materials typically is on the order of 32–35 degrees.

Another material that may be utilized is that formed of magnesium aluminometasilicate which may be represented by the general formula $$Al_2O_3 \cdot MgO \cdot 2SiO_2 \cdot nH_2O$$

wherein n satisfies the relationship $0 \leq n \leq 10$. Commercially available magnesium aluminometasilicates are sold as Grades $S_1$, $SG_1$, $UFL_2$, $US_2$, $FH_1$, $FH_2$, $FL_1$, $FL_2$, $S_2$, $SG_2$, $NFL_2N$, and $NS_2N$, under the trademark Neusilin™ by Fuji Chemical Industries (U.S.A.) Inc., Robbinsville, N.J. Especially preferred grades are $S_1$, $SG_1$, $US_2$ and $UFL_2$, with $US_2$ presently being most preferred. Those materials which are amorphous typically have a specific surface area (arca) of about 100–300 m$^2$/g, an oil absorption capacity of about 1.3–3.4 ml/g, a mean particle size of about 1–2 microns, an angle of repose about 25°–45°, a specific gravity of about 2 g/ml and a specific volume of about 2.1–12 ml/g.

Other absorptive materials may be substituted for the foregoing or blended therewith, such as for example, powders of microcrystalline cellulose sold under the tradenames Avicel (FMC Corporation) and Elcema (Degussa); porous sodium carboxymethyl cellulose crosslinked sold as Ac-Di-Sol (FMC Corporation); porous soy bean hull fiber sold under the tradename Fl-1 Soy Fiber (Fibred Group); and porous agglomerated silicon dioxide, sold under the tradenames Cab-O-Sil (Cabot) and Aerosil (Degussa).

The liquid, active agent formulation may be in any form that can be dispensed from the inside of the pores as the drug layer disintegrates in the environment of use. The formulation, for example, may be neat, liquid active agent, liquid active agent in a solution, suspension, emulsion or self-emulsifying composition, or the like, or a liposomal solution or solid formulation, or solid active agent in solution, suspension or slurry. Optionally other dosage-forming ingredients, such as an antioxidant, a suspending agent, a surface active agent, and the like may be present in the liquid, active agent formulation. The liquid, active agent formulation will be released in a form most suitable to provide active agent to the site of delivery in a state in which it may be rapidly absorbed in the environment of use to provide its beneficial action with minimum delay once delivered to the absorption site.

It often is desirable to provide the dosage form with a flow-promoting layer or lubricant that facilitates complete release of the drug layer from the compartment formed by the semipermeable wall since the formed bilayer tablet may be formed with surface irregularities that impede the release of the drug layer from the dosage form and sometimes results in incomplete release of the drug layer.

Dosage forms of this invention release effective amounts of active agent to the patient over a prolonged period of time and often provide the opportunity for less frequent dosing, including once-a-day dosing, than previously required for immediate release compositions. The dosage forms of this invention comprise a composition containing a liquid, active agent formulation contained in porous particles dispersed in a bioerodible carrier.

Active agents include, inter allia, foods, food supplements, nutrients, drugs, antiacids, vitamins, microorganism attenuators and other agents that provide a benefit in the environment of use and may be dissolved, suspended or otherwise dispersed in a liquid to form a liquid, active agent formulation. Active agents include any physiologically or pharmacologically active substance that produces a localized or systemic effect or effects in animals, including warm blooded mammals, humans and primates; domestic household or farm animals such as cats, dogs, sheep, goats, cattle, horses and pigs; laboratory animals such as mice, rats and guinea pigs; zoo and wild animals; and the like. Active agents that can be delivered include inorganic and organic compounds, including, without limitation, active agents which act on the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autacoid systems, the alimentary and excretory systems, the histamine system and the central nervous system.

Suitable active agents may be selected from, for example, proteins, enzymes, enzyme inhibitors, hormones, polynucleotides, nucleoproteins, polysaccharides, glycoproteins, lipoproteins, polypeptides, steroids, hypnotics and sedatives, psychic energizers, tranquilizers, anticonvulsants, antidepressants, muscle relaxants, antiparkinson agents, analgesics, anti-inflammatories, antihystamines, local anesthetics, muscle contractants, antimicrobials, antimalarials, antivirals, antibiotics, antiobesity agents, hormonal agents including contraceptives, sympathomimetics, polypeptides and proteins capable of eliciting physiological effects, diuretics, lipid regulating agents, antiandrogenic agents, antiparasitics, neoplastics, antineoplastics, antihyperglycemics, hypoglycemics, nutritional agents and supplements, growth supplements, fats, ophthalmics, antienteritis agents, electrolytes and diagnostic agents.

Examples of particular active agents useful in this invention include prochlorperazine edisylate, ferrous sulfate, albuterol, aminocaproic acid, mecamylamine hydrochloride, procainamide hydrochloride, amphetamine sulfate, methamphetamine hydrochloride, benzphetamine hydrochloride, isoproterenol sulfate, phenmetrazine hydrochloride, bethanechol chloride, methacholine chloride, pilocarpine hydrochloride, atropine sulfate, scopolamine bromide, isopropamide iodide, tridihexethyl chloride, phenformin hydrochloride, methylphenidate hydrochloride, theophylline cholinate, cephalexin hydrochloride, diphenidol, meclizine hydrochloride, prochlorperazine maleate, phenoxybenzamine, thiethylperazine maleate, anisindione, diphenadione erythrityl tetranitrate, digoxin, isoflurophate, acetazolamide, nifedipine, methazolamide, bendroflumethiazide, chlorpropamide, glipizide, glyburide, gliclazide, tobutamide, chlorproamide, tolazamide, acetohexamide, metformin, troglitazone, orlistat, bupropion, nefazodone, tolazamide, chlormadinone acetate, phenaglycodol, allopurinol, aluminum aspirin, methotrexate, acetyl sulfisoxazole, hydrocortisone, hydrocorticosterone acetate, cortisone acetate, dexamethasone and its derivatives such as betamethasone, triamcinolone, methyltestosterone, 17-β-estradiol, ethinyl estradiol, ethinyl estradiol 3-methyl ether, prednisolone, 17-β-hydroxyprogesterone acetate, 19-nor-progesterone, norgestrel, norethindrone, norethisterone, norethiederone, progesterone, norgesterone, norethynodrel, terfandine, fexofenadine, aspirin, acetaminophen, indomethacin, naproxen, fenoprofen, sulindac, indoprofen, nitroglycerin, isosorbide dinitrate, propranolol, timolol, atenolol, alprenolol, cimetidine, clonidine, imipramine, levodopa, selegiline, chlorpromazine, methyldopa, dihydroxyphenylalanine, calcium gluconate, ketoprofen, ibuprofen, cephalexin, erythromycin, haloperidol, zomepirac, ferrous lactate, vincamine, phenoxybenzamine, diltiazem, milrinone, captropril, mandol, quanbenz, hydrochlorothiazide, ranitidine, flurbiprofen, fenbufen, fluprofen, tolmetin, alclofenac, mefenamic, flufenamic, difuninal, nimodipine, nitrendipine, nisoldipine, nicardipine, felodipine, lidoflazine, tiapamil, gallopamil, amlodipine, mioflazine, lisinopril, enalapril, captopril, ramipril, enalaprilat, famotidine, nizatidine, sucralfate, etintidine, tetratolol, minoxidil, chlordiazepoxide, diazepam, amitriptyline, and imipramine, and pharmaceutical salts of these active agents. Further examples are proteins and peptides which include, but are not limited to, insulin, colchicine, glucagon, thyroid stimulating hormone, parathyroid and pituitary hormones, calcitonin, renin, prolactin, corticotrophin, thyrotropic hormone, follicle stimulating hormone, chorionic gonadotropin, gonadotropin releasing hormone, bovine somatotropin, porcine somatropin, oxytocin, vasopressin, prolactin, somatostatin, lypressin, pancreozymin, luteinizing hormone, LHRH, interferons, interleukins, growth hormones such as human growth hormone, bovine growth hormone and porcine growth hormone, fertility inhibitors such as the prostaglandins, fertility promoters, growth factors, and human pancreas hormone releasing factor.

The present invention has particular utility in the delivery of liquid, active agent formulations that are in the form of emulsions or self-emulsifying compositions. The term emulsion as used in this specification denotes a two-phase system in which one phase is finely dispersed in the other phase. The term emulsifier, as used by this invention, denotes an agent that can reduce and/or eliminate the surface and the interfacial tension in a two-phase system. The emulsifier agent, as used herein, denotes an agent possessing both hydrophilic and lipophilic groups in the emulsifier agent. The term microemulsion, as used herein, denotes a multicomponent system that exhibits a homogenous single phase in which quantities of a drug can be solubilized. Typically, a microemulsion can be recognized and distinguished from ordinary emulsions in that the microemulsion is more stable and usually substantially transparent. The term solution, as used herein, indicates a chemically and physically homogenous mixture of two or more substances.

The emulsion formulations of active agent generally comprise 0.5 wt % to 99 wt % of a surfactant. The surfactant functions to prevent aggregation, reduce interfacial tension between constituents, enhance the free-flow of constituents, and lessen the incidence of constituent retention in the dosage form. The therapeutic emulsion formulations useful in this invention may comprise a surfactant that imparts emulsification comprising a member selected from the group consisting of polyoxyethylenated castor oil comprising 9 moles of ethylene oxide, polyoxyethylenated castor oil comprising 15 moles of ethylene oxide, polyoxyethylene castor oil comprising 20 moles of ethylene oxide, polyoxyethylenated castor oil comprising 25 moles of ethylene oxide, polyoxyethylenated castor oil comprising 40 moles of ethylene oxide, polyoxylenated castor oil comprising 52 moles of ethylene oxide, polyoxyethylenated sorbitan monopalmitate comprising 20 moles of ethylene oxide, polyoxyethylenated sorbitan monolaurate comprising 20 moles of ethylene oxide, polyoxyethylenated sorbitan monooleate comprising 20 moles of ethylene oxide, polyoxyethylenated sorbitan monostearate comprising 20 moles of ethylene oxide, polyoxyethylenated sorbitan monostearate comprising 4 moles of ethylene oxide, polyoxyethylenated sorbitan tristearate comprising 20 moles of ethylene oxide, polyoxyethylenated sorbitan monostea rate comprising 20 moles of ethylene oxide, polyoxyethylenated sorbitan trioleate comprising 20 moles of ethylene oxide, polyoxyethylenated stearic acid comprising 8 moles of ethylene oxide, polyoxyethylene lauryl ether, polyoxyethylenated stearic acid comprising 40 moles of ethylene oxide, polyoxyethylenated stearic acid comprising 50 moles of ethylene oxide, polyoxyethylenated stearyl alcohol comprising 2 moles of ethylene oxide, and polyoxyethylenated oleyl alcohol comprising 2 moles of ethylene oxide. The surfactants are available from Atlas Chemical Industries, Wilmington, Del.; Drew Chemical Corp., Boonton, N.J.; and GAF Corp., New York, N.Y.

Typically, an active agent emulsified formulation useful in the invention initially comprises an oil phase. The oil phase of the emulsion comprises any pharmaceutically acceptable oil which is not miscible with water. The oil can be an edible liquid such as a non-polar ester of an unsaturated fatty acid, derivatives of such esters, or mixtures of such esters can be utilized for this purpose. The oil can be vegetable, mineral, animal or marine in origin. Examples of non-toxic oils comprise a member selected from the group consisting of peanut oil, cottonseed oil, sesame oil, olive oil, corn oil, almond oil, mineral oil, castor oil, coconut oil, palm oil, cocoa butter, safflower, a mixture of mono- and di-glycerides of 16 to 18 carbon atoms, unsaturated fatty acids, fractionated triglycerides derived from coconut oil, fractionated liquid triglycerides derived from short chain 10 to 15 carbon atoms fatty acids, acetylated monoglycerides, acetylated diglycerides, acetylated triglycerides, olein known also as glyceral trioleate, palmitin known as glyceryl tripalmitate, stearin known also as glyceryl tristearate, lauric acid hexylester, oleic acid oleylester, glycolyzed ethoxylated glycerides of natural oils, branched fatty acids with 13 molecules of ethyleneoxide, and oleic acid decylester. The concentration of oil, or oil derivative in the emulsion formulation is 1 wt % to 40 wt %, with the wt % of all constituents in the emulsion preparation equal to 100 wt %. The oils are disclosed in *Pharmaceutical Sciences by Remington*, $17^{th}$ Ed., pp. 403–405, (1985) published by Mark Publishing Co., in *Encyclopedia of Chemistry*, by Van Nostrand Reinhold, $4^{th}$ Ed., pp. 644–645, (1986) published by Van Nostrand Reinhold Co.; and in U.S. Pat. No. 4,259,323 issued to Ranucci.

The dosage form and method of this invention may be applied generally to liquid formulations of active agents, which may be prepared conventionally as described herein and, for example, to those liquid formulations contained in commercially-available dosage forms. Examples of commercially available encapsulated liquid formulations that may be utilized include, inter alia, Placidyl® brand of ethchlorvynol, Adalat® brand of nifedipine, VePesid® brand of etoposide, Lanoxicaps® brand of digoxin, Zantac® brand of ranitidine hydrochloride, Sandimmune® and Neoral® brands of cyclosporin, Calderol® brand of calcifediol, Zarontin® brand of ethosuximide, Procardia® brand of nifedipine, Rocaltrol® brand of calcitriol and Vescenoid® brand of tretinoin.

The dosage form may contain an antioxidant to slow or effectively stop the rate of any autoxidizable material present in the dosage form, particularly if it is in the form of a gelatin capsule. Representative antioxidants comprise a member selected from the group of ascorbic acid; alpha tocopherol; ascorbyl palmitate; ascorbates; isoascorbates; butylated hydroxyanisole; butylated hydroxytoluene; nordihydroguiaretic acid; esters of garlic acid comprising at least 3 carbon atoms comprising a member selected from the group consisting of propyl gallate, octyl gallate, decyl gallate, decyl gallate; 6-ethoxy-2,2,4-trimethyl-1,2-dihydroguinoline; N-acetyl-2,6-di-t-butyl-p-aminophenol; butyl tyrosine; 3-tertiarybutyl-4-hydroxyanisole; 2-tertiary-butyl-4-hydroxyanisole; 4-chloro-2,6-ditertiary butyl phenol; 2,6-ditertiary butyl p-methoxy phenol; 2,6-ditertiary butyl-p-cresol: polymeric antioxidants; trihydroxybutyro-phenone physiologically acceptable salts of ascorbic acid, erythorbic acid, and ascorbyl acetate; calcium ascorbate; sodium ascorbate; sodium bisulfite; and the like. The amount of antioxidant used for the present purposes is about 0.001% to 25% of the total weight of the composition present in the dosage form. Antioxidants are known to the prior art in U.S. Pat. Nos. 2,707,154; 3,573,936; 3,637,772; 4,038,434; 4,186,465 and 4,559,237.

The dosage form may also contain a chelating agent to protect the active agent either during storage or when in use. Examples of chelating agents include, for example, polyacrylic acid, citric acid, edetic acid, disodium edetic acid, and the like. The chelating agent may be co-delivered with the active agent in the environment of use to preserve and protect the active agent in situ. Protection is provided for active agents which are inactivated by chelation with multivalent metal cations such as calcium, magnesium or aluminum that may be present in some foods and are at natural background levels in the fluids of the gastrointestinal tract. Such chelating agents may be combined with the liquid, active agent formulation in the porous particles, or the chelating agents may be incorporated into the drug layer in which the porous particles are dispersed.

The liquid formulation may also comprise a surfactant or a mixture of surfactants where the surfactant is selected from the group consisting of nonionic, anionic and cationic surfactants. Exemplary nontoxic, nonionic surfactants suitable for forming a composition comprise alkylated aryl polyether alcohols known as Triton®; polyethylene glycol tertdodecyl throether available as Nonic®; fatty and amide condensate or Alrosol®; aromatic polyglycol ether condensate or Neutronyx®; fatty acid alkanolamine or Ninol® sorbitan monolaurate or Span®; polyoxyethylene sorbitan esters or Tweens®; sorbitan monolaurate polyoxyethylene or Tween 20®; sorbitan mono-oleate polyoxyethylene or Tween 80®; polyoxypropylene-polyoxyethylene or Pluronic®; polyglycolyzed glycerides such as Labraosol, polyoxyethylated castor oil such as Cremophor and polyoxypropylene-polyoxyethylene-8500 or Pluronic®. By way of example, anionic surfactants comprise sulfonic acids and the salts of sulfonated esters such as sodium lauryl sulfate, sodium sulfoethyl oleate, dioctyl sodium sulfosuccinate, cetyl sulfate sodium, myristyl sulfate sodium; sulated esters; sulfated amides; sulfated alcohols; sulfated ethers; sulfated carboxylic acids; sulfonated aromatic hydrocarbons; sulfonated ethers; and the like. The cationic surface active agents comprise cetyl pyridinium chloride; cetyl trimethyl ammonium bromide; diethylmethyl cetyl ammonium chloride; benzalkonium chloride; benzethonium chloride; primary alkylamonium salts; secondary alkylamonium salts; tertiary alkylamonium salts; quaternary alkylamonium salts; acylated polyamines; salts of heterocyclic amines; palmitoyl carnitine chloride, behentriamonium methosulfate, and the like. Generally, from 0.01 part to 1000 parts by weight of surfactant, per 100 parts of active agent is admixed with the active agent to provide the active agent formulation. Surfactants are known to the prior art in U.S. Pat. Nos. 2,805,977; and in 4,182,330.

The liquid formulation may comprise permeation enhancers that facilitate absorption of the active agent in the environment of use. Such enhancers may, for example, open the so-called "tight junctions" in the gastrointestinal tract or modify the effect of cellular components, such a p-glycoprotein and the like. Suitable enhancers include alkali metal salts of salicyclic acid, such as sodium salicylate, caprylic or capric acid, such as sodium caprylate or sodium caprate, and the like. Enhancers may include the bile salts, such as sodium deoxycholate. Various p-glycoprotein modulators are described in U.S. Pat. Nos. 5,112,817 and 5,643,909, which are incorporated herein by reference. Various other absorption enhancing compounds and materials are described in U.S. Pat. No. 5,824,638, which also is incorporated herein by reference. Enhancers may be used either alone or as mixtures in combination with other enhancers.

The liquid, active agent formulation of the dosage form may optionally be formulated with inorganic or organic acids or salts of drugs which promote dissolution and disintegration or swelling of the porous particles upon contact with biological fluids. The acids serve to lower the pH of the microenvironment at the porous particle, and promote rapid dissolution of a particle, such as calcium hydrogen phosphate, that is soluble in low pH environments, thus providing rapid liberation of the liquid, active agent formulation contained in the porous particle. Examples of organic acids include citric acid, tartaric acid, succinic acid, malic acid, fumaric acid and the like. Salts of drugs where the anion of the salt is acidic, such as acetate, hydrochloride, hydrobromide, sulfate, succinate, citrate, and the like, can be utilized to produce immediate disintegration and dissolution of the porous particle. A more complete list of acidic components for this application is provided in Journal of Pharmaceutical Sciences, "Pharmaceutical Salts", Review Articles, January, (1977), Vol. 66, No. 1, pages 1–19. The interaction of an acidic component with a porous particle of, for example, calcium hydrogen phosphate, in the presence of water from gastric fluids accelerates dissolution of the particle at a greater rate than gastric fluid alone, producing a more rapid and complete release of the liquid, active agent formulation into the environment of use. Likewise alkaline components or salts of drugs where the cation of the salt is alkaline such as choline may be incorporated into the liquid, active agent formulation to promote rapid and complete dissolution of a porous particle which is soluble or swells at elevated pH. Such a particle may be formed, for example, of poly(methacrylic acid-methyl methacrylate) 1:2 available commercially as Eudragit S100 (Rohm America, Sommerset, N.J.).

With reference to FIG. 1, a porous particle 10 is illustrated having a material mass 12 that defines a plurality of pores 14. Within the pores 14 is sorbed a liquid, active agent formulation designated as 16. Pores 14 extend from the external surface of the particle and into the interior. Pores are open on the surface to permit the liquid, active agent formulation to be sorbed into the particles by conventional mixing techniques such as wet granulation, spraying of the liquid, active agent formulation onto a fluidized bed of the particles, or the like.

Figure 2:
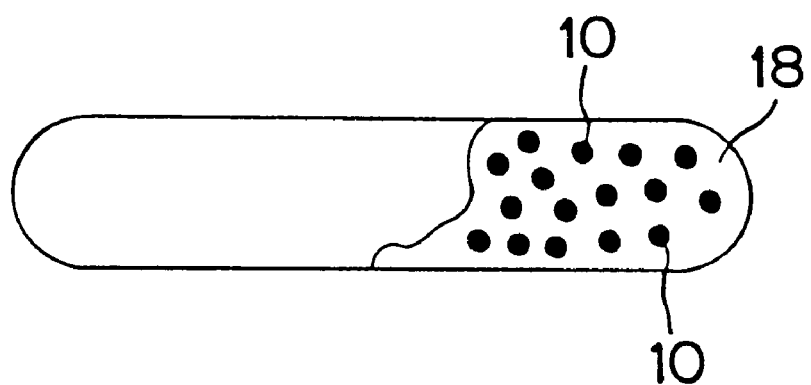
FIG. 2 illustrates a composition comprising a plurality of particles containing liquid, active agent formulation as illustrated in FIG. 1 dispersed in a carrier and suitable for use in the dosage forms of the invention.

In FIG. 2, a composition is illustrated which contains the porous particles 10 dispersed within a carrier 18. Typically, the composition is compacted as a tablet to form the drug layer portion of the dosage form. During the compacting phase of the manufacture, it is desired that the particle mass 12 be sufficiently non-friable so as to resist pulverization or crushing and undesired exudation of the liquid, active agent formulation.

Figure 3:
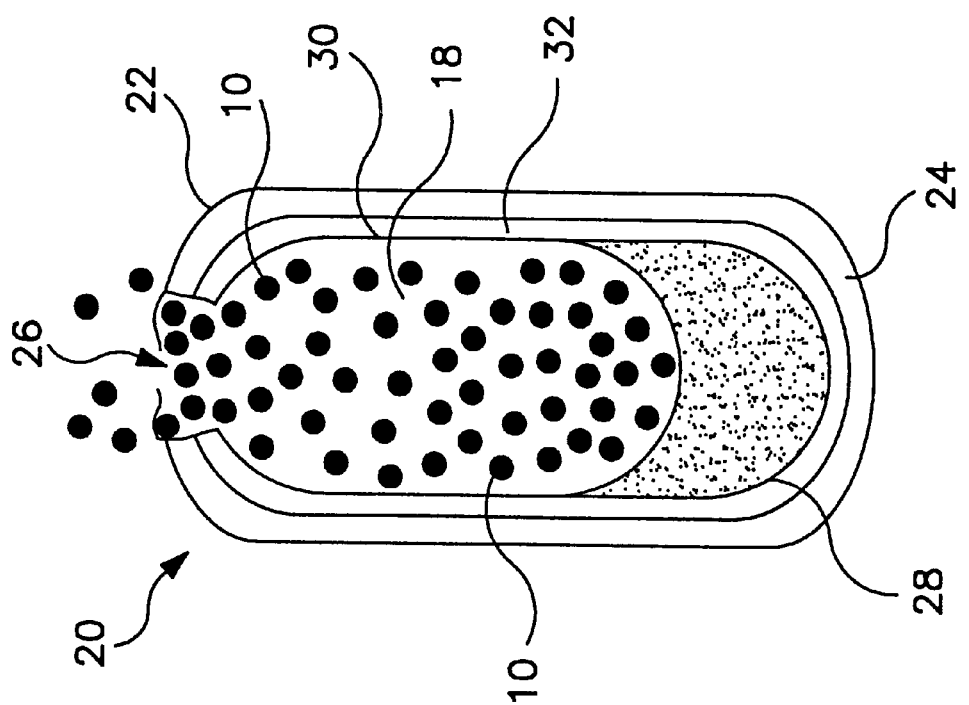
FIG. 3 illustrates a dosage form of this invention adapted for zero order release of active agent.

A dosage form 20 intended for continuous, zero order release of the active agent is illustrated in FIG. 3. As can be seen therein, the dosage form 20 comprises a wall 22 defining a cavity 24. Wall 22 is provided with an exit orifice 26. Within cavity 24 and remote from the exit orifice 26 is a push layer 28. A drug layer 30 is located within cavity 24 adjacent exit orifice 26. A plurality of porous particles 10 is dispersed in carrier 18 within the cavity 24 to form the drug layer 30. An optional, flow-promoting layer 32, the function of which will be described and which may be formed as a secondary wall, extends between drug layer 30 and the inner surface of wall 22. An orifice 26 is provided at one end of dosage form 20 to permit expression of the drug layer 30 from the dosage form upon expansion of push layer 28.

The wall 22 is formed to be permeable to the passage of an external fluid, such as water and biological fluids, and it is substantially impermeable to the passage of active agent, osmagent, osmopolymer and the like. As such, it is semipermeable. The selectively semipermeable compositions used for forming the wall are essentially nonerodible and they are insoluble in biological fluids during the life of the dosage form. Wall 22 need not be semipermeable in its entirety, but at least a portion of wall 22 should be semipermeable to allow fluid to contact or communicate with push layer 28 such that push layer 28 imbibes fluid during use. Specific materials for the fabrication of semipermeable wall 22 are well known in the art, and representative examples of such materials are described later herein.

Secondary wall 32, which functions as the flow-promoting layer or lubricant, is in contacting position with the inner surface of the semipermeable wall 22 and at least the external surface of the drug layer that is opposite wall 22; although the secondary wall 32 may, and preferably will, extend to, surround and contact the external surface of the push layer. Wall 32 typically will surround at least that portion of the external surface of the drug layer that is opposite the internal surface of wall 22. Secondary wall 32 may be formed as a coating applied over the compressed core comprising the drug layer and the push layer. The outer semipermeable wall 22 surrounds and encases the inner, secondary wall 32. Secondary wall 32 is preferably formed as a subcoat of at least the surface of the drug layer 30, and optionally the entire external surface of the compacted drug layer 30 and the push layer 28. When the semipermeable wall 22 is formed as a coat of the composite formed from the drug layer 30, the push layer 28 and the secondary wall 32, contact of the semipermeable wall 22 with the inner coat is assured.

Figure 4:
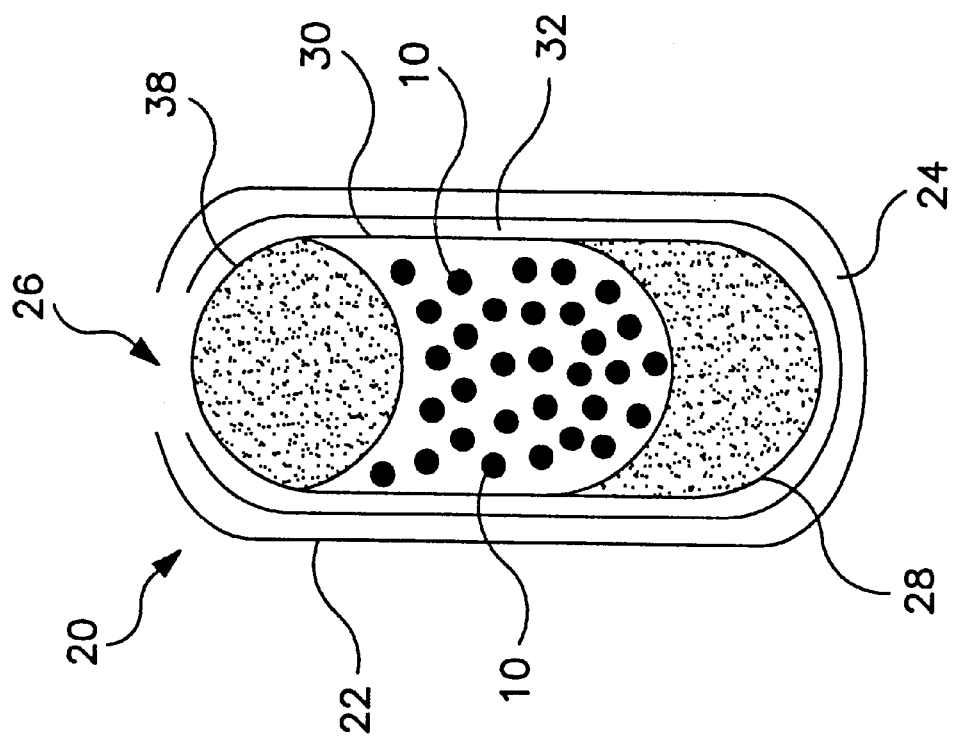
FIG. 4 illustrates a dosage form of this invention adapted to deliver a delayed pulse of the active agent.

FIG. 4 illustrates another form of the invention wherein the dosage form 20 includes a placebo layer 38 which serves to delay release of particles 10 in the environment of use. The other components of the dosage form 20 are substantially the same as those described with reference to FIG. 3, and like components are designated with the same reference numerals. The extent of the delay that may be afforded by the placebo layer will in part depend on the volume of the placebo layer 38 which has to be displaced by the push layer 28 as it imbibes fluid and expands. FIGS. 6–10 illustrate different periods of delay that may be obtained by varying the placebo layer 38 when delivering a representative compound progesterone. The dosage forms for which the results in FIGS. 6–10 are illustrated correspond to those described in Examples 4–8, respectively. Delays of 2 hours to 10 hours are illustrated.

Representative polymers for forming wall 22 comprise semipermeable homopolymers, semipermeable copolymers, and the like. Such materials comprise cellulose esters, cellulose ethers and cellulose ester-ethers. The cellulosic polymers have a degree of substitution (DS) of their anhydroglucose unit of from greater than 0 up to 3, inclusive. Degree of substitution (DS) means the average number of hydroxyl groups originally present on the anhydroglucose unit that are replaced by a substituting group or converted into another group. The anhydroglucose unit can be partially or completely substituted with groups such as acyl, alkanoyl, alkenoyl, aroyl, alkyl, alkoxy, halogen, carboalkyl, alkylcarbamate, alkylcarbonate, alkylsulfonate, alkysulfamate, semipermeable polymer forming groups, and the like, wherein the organic moieties contain from one to twelve carbon atoms, and preferably from one to eight carbon atoms.

The semipermeable compositions typically include a member selected from the group consisting of cellulose acylate, cellulose diacylate, cellulose triacylate, cellulose acetate, cellulose diacetate, cellulose triacetate, mono-, di- and tri-cellulose alkanylates, mono-, di-, and tri-alkenylates, mono-, di-, and tri-aroylates, and the like. Exemplary polymers include cellulose acetate having a DS of 1.8 to 2.3 and an acetyl content of 32 to 39.9%; cellulose diacetate having a DS of 1 to 2 and an acetyl content of 21 to 35%; cellulose triacetate having a DS of 2 to 3 and an acetyl content of 34 to 44.8%; and the like. More specific cellulosic polymers include cellulose propionate having a DS of 1.8 and a propionyl content of 38.5%; cellulose acetate propionate having an acetyl content of 1.5 to 7% and an acetyl content of 39 to 42%; cellulose acetate propionate having an acetyl content of 2.5 to 3%, an average propionyl content of 39.2 to 45%, and a hydroxyl content of 2.8 to 5.4%; cellulose acetate butyrate having a DS of 1.8, an acetyl content of 13 to 15%, and a butyryl content of 34 to 39%; cellulose acetate butyrate having an acetyl content of 2 to 29%, a butyryl content of 17 to 53%, and a hydroxyl content of 0.5 to 4.7%; cellulose triacylates having a DS of 2.6 to 3, such as cellulose trivalerate, cellulose trilamate, cellulose tripalmitate, cellulose trioctanoate and cellulose tripropionate; cellulose diesters having a DS of 2.2 to 2.6, such as cellulose disuccinate, cellulose dipalmitate, cellulose dioctanoate, cellulose dicaprylate, and the like; and mixed cellulose esters, such as cellulose acetate valerate, cellulose acetate succinate, cellulose propionate succinate, cellulose acetate octanoate, cellulose valerate palmitate, cellulose acetate heptanoate, and the like. Semipermeable polymers are known in U.S. Pat. No. 4,077,407, and they can be synthesized by procedures described in Encyclopedia of Polymer Science and Technology, Vol. 3, pp. 325–354 (1964), Interscience Publishers Inc., New York, N.Y.

Additional semipermeable polymers for forming the outer wall 22 comprise cellulose acetaldehyde dimethyl acetate; cellulose acetate ethylcarbamate; cellulose acetate methyl carbamate; cellulose dimethylaminoacetate; semipermeable polyamide; semipermeable polyurethanes; semipermeable sulfonated polystyrenes; cross-linked selectively semipermeable polymers formed by the coprecipitation of an anion and a cation, as disclosed in U.S. Pat. Nos. 3,173,876; 3,276,586; 3,541,005; 3,541,006 and 3,546,142; semipermeable polymers, as disclosed by Loeb, et al. in U.S. Pat. No. 3,133,132; semipermeable polystyrene derivatives; semipermeable poly(sodium styrenesulfonate); semipermeable poly(vinylbenzyltrimethylammonium chloride); and semipermeable polymers exhibiting a fluid permeability of $10^{-5}$ to $10^{-2}$ (cm. mil/atm. hr), expressed as per atmosphere of hydrostatic or osmotic pressure differences across a semipermeable wall. The polymers are known to the art in U.S. Pat. Nos. 3,845,770; 3,916,899 and 4,160,020; and in Handbook of Common Polymers, Scott and Roff (1971) CRC Press, Cleveland, Ohio.

Wall 22 also can comprise a flux regulating agent. The flux regulating agent is a compound added to assist in regulating the fluid permeability or flux through wall 22. The flux regulating agent can be a flux enhancing agent or a decreasing agent. The agent can be preselected to increase or decrease the liquid flux. Agents that produce a marked increase in permeability to fluid such as water, are often essentially hydrophilic, while those that produce a marked decrease to fluids such as water, are essentially hydrophobic. The amount of regulator in the wall when incorporated therein generally is from about 0.01% to 20% by weight or more. The flux regulator agents in one embodiment that increase flux include polyhydric alcohols, polyalkylene glycols, poilyalkylenediols, polyesters of alkylene glycols, and the like. Typical flux enhancers include polyethylene glycol 300, 400, 600, 1500, 4000, 6000 and the like; low molecular weight gylcols such as polypropylene glycol, polybutylene glycol and polyamylene glycol: the polyalkylenediols such as poly(1,3-propanediol), poly(1,4-butanediol), poly(1,6-hexanediol), and the like; aliphatic diols such as 1,3-butylene glycol, 1,4-pentamethylene glycol, 1,4-hexamethylene glycol, and the like; alkylene triols such as glycerine, 1,2,3-butanetriol, 1,2,4-hexanetriol, 1,3,6-hexanetriol and the like; esters such as ethylene glycol dipropionate, ethylene glycol butyrate, butylene glycol dipropionate, glycerol acetate esters, and the like. Representative flux decreasing agents include phthalates substituted with an alkyl or alkoxy or with both an alkyl and alkoxy group such as diethyl phthalate, dimethoxyethyl phthalate, dimethyl phthalate, and [di(2-ethylhexyl) phthalate], aryl phthalates such as triphenyl phthalate, and butyl benzyl phthalate; insoluble salts such as calcium sulphate, barium sulphate, calcium phosphate, and the like; insoluble oxides such as titanium oxide; polymers in powder, granule and like form such as polystyrene, polymethylmethacrylate, polycarbonate, and polysulfone; esters such as citric acid esters esterfied with long chain alkyl groups; inert and substantially water impermeable fillers; resins compatible with cellulose based wall forming materials, and the like.

Other materials that can be used to form the wall 22 for imparting flexibility and elongation properties to the wall, for making wall 22 less-to-nonbrittle and to render tear strength, include phthalate plasticizers such as dibenzyl phthalate, dihexyl phthalate, butyl octyl phthalate, straight chain phthalates of six to eleven carbons, di-isononyl phthalte, di-isodecyl phthalate, and the like. The plasticizers include nonphthalates such as triacetin, dioctyl azelate, epoxidized tallate, tri-isoctyl trimellitate, tri-isononyl trimellitate, sucrose acetate isobutyrate, epoxidized soybean oil, and the like. The amount of plasticizer in a wall when incorporated therein is about 0.01% to 20% weight, or higher.

The drug layer 30 may comprise a composition formed of a liquid active agent formulation absorbed in porous particles, the preferred characteristics of the particles being described elsewhere herein, and a carrier 18. Depending on the release characteristics desired, the carrier may be a binder, which may be a hydrophilic polymer. The hydrophilic polymer provides a hydrophilic polymer composition in the drug layer that may contribute to the uniform release rate of active agent and controlled delivery pattern by controlling the rate of release of the porous particles containing the liquid, active agent formulation from the dosage form over a sustained period of time. Representative examples of these polymers are poly(alkylene oxide) of 100,000 to 750,000 number-average molecular weight, including poly(ethylene oxide), poly(methylene oxide), poly (butylene oxide) and poly(hexylene oxide); and a poly (carboxymethylcellulose) of 40,000 to 400,000 number-average molecular weight, represented by poly(alkali carboxymethylcellulose), poly(sodium carboxymethylcellulose), poly(potassium carboxymethylcellulose) and poly(lithium carboxymethylcellulose). The drug composition can comprise a hydroxypropylalkylcellulose of 9,200 to 125,000 number-average molecular weight for enhancing the delivery properties of the dosage form as represented by hydroxypropylethylcellulose, hydroxypropyl methylcellulose, hydroxypropylbutylcellulose and hydroxypropylpentylcellulose; and a poly(vinylpyrrolidone) of 7,000 to 360,000 number-average molecular weight for enhancing the flow properties of the dosage form. Preferred among those polymers are the poly(ethylene oxide) of 100,000–300,000 number average molecular weight. Carriers that erode in the gastric environment, i.e., bioerodible carriers, are especially preferred.

Surfactants and disintegrants may be utilized in the carrier as well. Exemplary of the surfactants are those having an HLB value of between about 10–25, such as polyethylene glycol 400 monostearate, polyoxyethylene-4-sorbitan monolaurate, polyoxyethylene-20-sorbitan monooleate, polyoxyethylene-20-sorbitan monopalmitate, polyoxyethylene-20-monolaurate, polyoxyethylene-40-stearate, sodium oleate and the like. Disintegrants may be selected from starches, clays, celluloses, algins and gums and crosslinked starches, celluloses and polymers. Representative disintegrants include corn starch, potato starch, croscarmelose, crospovidone, sodium starch glycolate, Veegum HV, methylcellulose, agar, bentonite, carboxymethylcellulose, alginic acid, guar gum and the like.

In those cases where rapid release of drug is desired, the carrier in the drug layer may be eliminated or present in only small amounts, and may comprise a binder and/or disintegrant. Representative formulations of such dosage forms are described in more detail in Examples 7 and 8 for the materials calcium hydrogen phosphate and magnesium aluminometasilicate.

The drug layer 30 may be formed as a mixture containing the porous particles and the carrier. The carrier portion of the drug layer may be formed from particles by comminution that produces the desired size of the carrier particle used in the fabrication of the drug layer. The means for producing carrier particles include granulation, spray drying, sieving, lyophilization, crushing, grinding, jet milling, micronizing and chopping to produce the intended micron particle size. The process can be performed by size reduction equipment, such as a micropulverizer mill, a fluid energy grinding mill, a grinding mill, a roller mill, a hammer mill, an attrition mill, a chaser mill, a ball mill, a vibrating ball mill, an impact pulverizer mill, a centrifugal pulverizer, a coarse crusher and a fine crusher. The size of the particle can be ascertained by screening, including a grizzly screen, a flat screen, a vibrating screen, a revolving screen, a shaking screen, an oscillating screen and a reciprocating screen. The processes and equipment for preparing drug and carrier particles are disclosed in Pharmaceutical Sciences, Remington, 17th Ed., pp. 1585–1594 (1985); Chemical Engineers Handbook, Perry, 6th Ed., pp. 21–13 to 21–19 (1984); Journal of Pharmaceutical Sciences, Parrot, Vol. 61, No. 6, pp. 813–829 (1974); and Chemical Engineer, Hixon, pp. 94–103 (1990).

The active compound may be provided in the liquid active agent formulation in amounts of from 1 microgram to 5000 mg per dosage form, depending upon the required dosing level that must be maintained over the delivery period, i.e., the time between consecutive administrations of the dosage forms. More typically, loading of compound in the dosage forms will provide doses of compound to the subject ranging from 1 microgram to 2500 mg per day, more usually 1 mg to 2500 mg per day. The drug layer typically will be a substantially dry composition formed by compression of the carrier and the porous particles, with the understanding that the porous particles will have contained therein the liquid, active agent formulation. The push layer will push the drug layer from the exit orifice as the push layer imbibes fluid from the environment of use, and the exposed drug layer will be eroded to release the porous particles into the environment of use. This may be seen with reference to FIG. 3.

The push layer 28 is an expandable layer having a push-displacement composition in direct or indirect contacting layered arrangement with the drug layer 30. When in indirect contacting layered arrangement, an inert element (not shown), such as a spacer layer or disk, may be placed between the drug layer and the push layer. If several pulses of active agent are to be delivered from a single dosage form, similar inert layers may be interposed between discrete portions of drug layer. The inert layer(s) may be sized to provide appropriate time delay(s) between pulses of active agent and the volume of each discrete drug layer will provide control of the time period over which the pulse of active agent is delivered. Inert layers may be formed of materials utilized to form the push layer 28, or if desired, formed of materials that are easily compacted but do not swell in the fluid environment of use.

Push layer 28 comprises a polymer that imbibes an aqueous or biological fluid and swells to push the drug composition through the exit means of the device. Representatives of fluid-imbibing displacement polymers comprise members selected from poly(alkylene oxide) of 1 million to 15 million number-average molecular weight, as represented by poly(ethylene oxide) and poly(alkali carboxymethylcellulose) of 500,000 to 3,500,000 number-average molecular weight, wherein the alkali is sodium, potassium or lithium. Examples of additional polymers for the formulation of the push-displacement composition comprise osmopolymers comprising polymers that form hydrogels, such as Carbopol® acidic carboxypolymer, a polymer of acrylic cross-linked with a polyallyl sucrose, also known as carboxypolymethylene, and carboxyvinyl polymer having a molecular weight of 250,000 to 4,000,000; Cyanamer® polyacrylamides; cross-linked water swellable indenemaleic anhydride polymers; Good-rite® polyacrylic acid having a molecular weight of 80,000 to 200,000; Aqua-Keeps® acrylate polymer polysaccharides composed of condensed glucose units, such as diester cross-linked polygluran; and the like. Representative polymers that form hydrogels are known to the prior art in U.S. Pat. No. 3,865,108, issued to Hartop; U.S. Pat. No. 4,002,173, issued to Manning; U.S. Pat. No. 4,207,893, issued to Michaels; and in Handbook of Common Polymers, Scott and Roff, Chemical Rubber Co., Cleveland, Ohio.

The osmagent, also known as osmotic solute and osmotically effective agent, which exhibits an osmotic pressure gradient across the outer wall and subcoat, comprises a member selected from the group consisting of sodium chloride, potassium chloride, lithium chloride, magnesium sulfate, magnesium chloride, potassium sulfate, sodium sulfate, lithium sulfate, potassium acid phosphate, mannitol, urea, inositol, magnesium succinate, tartaric acid raffinose, sucrose, glucose, lactose, sorbitol, inorganic salts, organic salts and carbohydrates.

Use of the inner wall or subcoat 32 is optional, but presently preferred. The inner subcoat 32 typically may be 0.01 to 5 mm thick, more typically 0.025–0.25 mm thick, although a thicker subcoat, for example 0.5 to 5 mm thick, may be used in certain applications. The inner subcoat 32 comprises a member selected from hydrogels, gelatin, low molecular weight polyethylene oxides, e.g., less than 100,000 MW, hydroxyalkylcelluloses, e.g., hydroxyethylcellulose, hydroxypropylcellulose, hydroxyisopropylcelluose, hydroxybutylcellulose and hydroxyphenylcellulose, and hydroxyalkyl alkylcelluloses, e.g., hydroxypropyl methylcellulose, and mixtures thereof. The hydroxyalkylcelluloses comprises polymers having a 9,500 to 1,250,000 number-average molecular weight. For example, hydroxypropyl celluloses having number average molecular weights of between 80,000 to 850,000 are useful. The flow promoting layer may be prepared from conventional solutions or suspensions of the aforementioned materials in aqueous solvents or inert organic solvents. Prefered materials for the subcoat or flow promoting layer include hydroxypropyl cellulose, hydroxyethyl cellulose, hydroxypropyl methyl cellulose, povidone [poly(vinylpyrrolidone)], polyethylene glycol, and mixtures thereof. More prefered are mixtures of hydroxypropyl cellulose and povidone, prepared in organic solvents, particularly organic polar solvents such as lower alkanols having 1–8 carbon atoms, preferably ethanol, mixtures of hydroxyethyl cellolose and hydroxypropyl methyl cellulose prepared in aqueous solution, and mixtures of hydroxyetyyl cellulose and polyethylene glycol prepared in aqueous solution. Most preferably, the subcoat consists of a mixture of hydroxypropyl cellulose and povidone prepared in ethanol. Conveniently, the weight of the subcoat applied to the bilayer core may be correlated with the thickness of the subcoat and residual drug remaining in a dosage form in a release rate assay such as described herein. During manufacturing operations, the thickness of the subcoat may be controlled by controlling the weight of the subcoat taken up in the coating operation. When wall 32 is fabricated of a gel-forming material, contact with water in the environment of use facilitates formation of a gel or gel-like inner coat having a viscosity that may promote and enhance slippage between outer wall 22 and drug layer 30.

Exemplary solvents suitable for manufacturing the respective walls, layers, coatings and subcoatings utilized in the dosage forms of the invention comprise aqueous and inert organic solvents that do not adversely harm the materials utilized to fabricate the dosage forms. The solvents broadly include members selected from the group consisting of aqueous solvents, alcohols, ketones, esters, ethers, aliphatic hydrocarbons, halogenated solvents, cycloaliphatics, aromatics, heterocyclic solvents and mixtures thereof. Typical solvents include acetone, diacetone alcohol, methanol, ethanol, isopropyl alcohol, butyl alcohol, methyl acetate, ethyl acetate, isopropyl acetate, n-butyl acetate, methyl isobutyl ketone, methyl propyl ketone, n-hexane, n-heptane, ethylene glycol monoethyl ether, ethylene glycol monoethyl acetate, methylene dichloride, ethylene dichloride, propylene dichloride, carbon tetrachloride nitroethane, nitropropane tetrachloroethane, ethyl ether, isopropyl ether, cyclohexane, cyclooctane, benzene, toluene, naphtha, 1,4-dioxane, tetrahydrofuran, diglyme, water, aqueous solvents containing inorganic salts such as sodium chloride, calcium chloride, and the like, and mixtures thereof such as acetone and water, acetone and methanol, acetone and ethyl alcohol, methylene dichloride and methanol, and ethylene dichloride and methanol.

Pan coating may be conveniently used to provide the completed dosage form, except for the exit orifice. In the pan coating system, the subcoat on the wall-forming compositions is deposited by successive spraying of the respective composition on the bilayered core comprising the drug layer and the push layer accompanied by tumbling in a rotating pan. A pan coater is used because of its availability at commercial scale. Other techniques can be used for coating the drug core. Finally, the wall or coated dosage form are dried in a forced-air oven, or in a temperature and humidity controlled oven to free the dosage form of solvent. Drying conditions will be conventionally chosen on the basis of available equipment, ambient conditions, solvents, coatings, coating thickness, and the like.

Other coating techniques can also be employed. For example, the semipermeable wall and the subcoat of the dosage form can be formed in one technique using the air-suspension procedure. This procedure consists of suspending and tumbling the bilayer core in a current of air, an inner subcoat composition and an outer semipermeable wall forming composition, until, in either operation, the subcoat and the outer wall coat is applied to the bilayer core. The air-suspension procedure is well suited for independently forming the wall of the dosage form. The air-suspension procedure is described in U.S. Pat. No. 2,799,241; in J. Am. Pharm. Assoc., Vol. 48, pp. 451–459 (1959); and, ibid., Vol. 49, pp. 82–84 (1960). The dosage form also can be coated with a Wurster® air-suspension coater using, for example, methylene dichloride methanol as a cosolvent. An Aeromatic® air-suspension coater can be used employing a cosolvent.

The dosage form of the invention may be manufactured by standard techniques. For example, the dosage form may be manufactured by the wet granulation technique. In the wet granulation technique a solution, suspension or dispersion of the active agent in a liquid is mixed with the porous particles to allow the liquid, active agent formulation to sorb into the pores of the porous particles. Then the carrier is blended with the porous particles using an organic solvent, such as denatured anhydrous ethanol, as the granulation fluid. After a wet blend is produced, the wet mass blend is forced through a predetermined screen onto trays. The blend is dried under ambient conditions until the desired moisture level is obtained. The drying conditions are not so severe, however, that the liquid of the liquid, active agent formulation is allowed to evaporate to any significant extent. Next, a lubricant such as magnesium stearate or agglomerated silicon dioxide (Cab-O-Sil) for example, is added to the blend, which is then put into milling jars and mixed on a jar mill for several minutes. The composition is pressed into a layer, for example, in a Manesty® press. The first compressed layer is typically the drug layer, and then the push layer may be pressed against the composition forming the drug layer, and the bilayer tablets are fed to the Kilian® Dry Coater and surrounded with the drug-free coat, followed by the exterior wall solvent coating. In those instances where a trilayer dosage form for pulsatile release having a placebo layer is to be fabicated, the placebo layer is usually formed first, then the drug layer is pressed onto the placebo layer to form a bilayer composition, and then the push layer is compressed onto the bilayer core to form the trilayer composition. The trilayer tablet is then provided with the option subcoat and the membrane coat for the rate controlling membrane. It is apparent, however, that the order in which the respective layers are compressed may be different, but the foregoing is preferred.

In another manufacture the porous particles containing the liquid, active agent formulation and other ingredients comprising the drug layer are blended and pressed into a solid layer. The layer possesses dimensions that correspond to the internal dimensions of the area the layer is to occupy in the dosage form, and it also possesses dimensions corresponding to the second layer for forming a contacting arrangement therewith. The drug layer components can also be blended with a solvent and mixed into a solid or semisolid form by conventional methods, such as ballmilling, calendering, stirring or rollmilling, and then pressed into a preselected shape. Next, the expandable layer, e.g., a layer of osmopolymer composition, is placed in contact with the layer of drug in a like manner. The layering of the drug formulation and the osmopolymer layer can be fabricated by conventional two-layer press techniques. The two contacted layers are first coated with the flow-promoting subcoat and then an outer semipermeable wall. The air-suspension and air-tumbling procedures comprise in suspending and tumbling the pressed, contacting first and second layers in a current of air containing the delayed-forming composition until the first and second layers are surrounded by the wall composition.

The dosage form of the invention is provided with at least one exit orifice. The exit orifice cooperates with the drug core for the uniform release of drug from the dosage form. The exit orifice can be provided during the manufacture of the dosage form or during drug delivery by the dosage form in a fluid environment of use. The expression "exit orifice" as used for the purpose of this invention includes a member selected from the group consisting of a passageway; an aperture; an orifice; and a bore. The expression also includes an orifice that is formed from a substance or polymer that erodes, dissolves or is leached from the outer coat or wall or inner coat to form an exit orifice. The substance or polymer may include an erodible poly(glycolic) acid or poly(lactic) acid in the outer or inner coats; a gelatinous filament; a water-removable poly(vinyl alcohol); a leachable compound, such as a fluid removable pore-former selected from the group consisting of inorganic and organic salt, oxide and carbohydrate. An exit, or a plurality of exits, can be formed by leaching a member selected from the group consisting of sorbitol, lactose, fructose, glucose, mannose, galactose, talose, sodium chloride, potassium chloride, sodium citrate and mannitol to provide a uniform-release dimensioned pore-exit orifice. The exit orifice can have any shape, such as round, triangular, square, elliptical and the like for the uniform metered dose release of a drug from the dosage form. The dosage form can be constructed with one or more exits in spaced apart relation or one or more surfaces of the dosage form. The exit orifice can be performed by drilling, including mechanical and laser drilling, through the outer coat, the inner coat, or both. Exits and equipment for forming exits are disclosed in U.S. Pat. Nos. 3,845,770 and 3,916,899, by Theeuwes and Higuchi; in U.S. Pat. No. 4,063,064, by Saunders, et al.; and in U.S. Pat. No. 4,088,864, by Theeuwes, et al. The exit orifice may be from 10% to 100% of the inner diameter of the compartment formed by wall 22, preferably from 30% to 100%, and most preferably from 50% to 100%.

Figure 5:
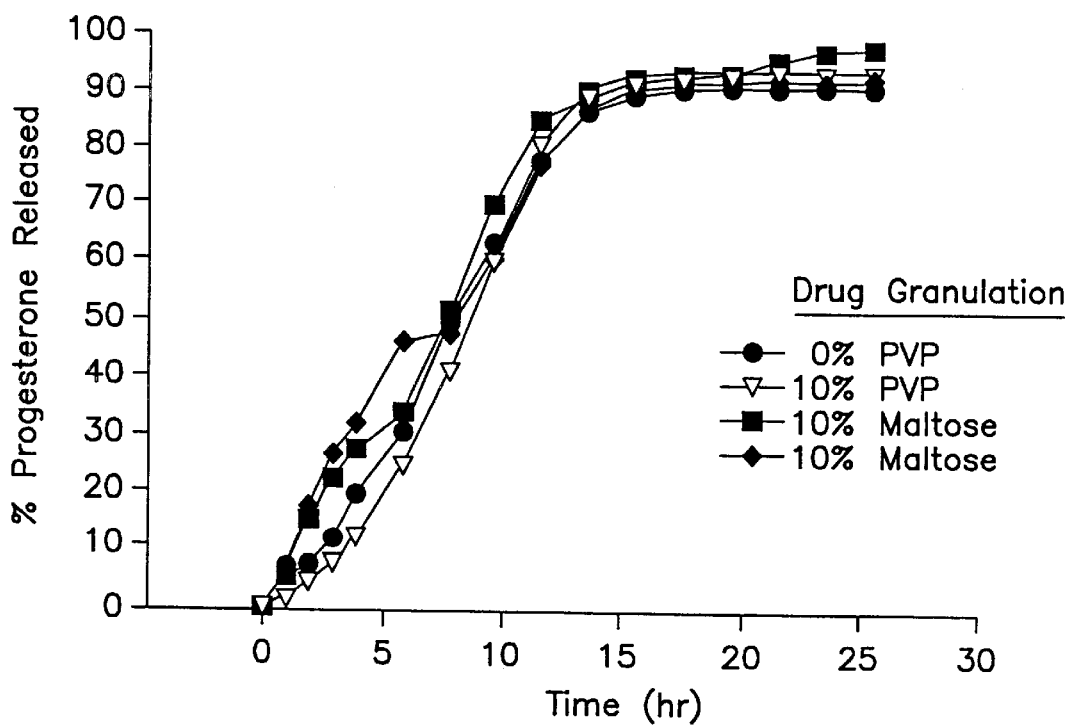
FIG. 5 illustrates the release profile (cumulative release as a function of time) of the active agent progesterone from a representative dosage form of the invention having zero order release rate.

The continuous release dosage forms provide a uniform rate of release of compound over a prolonged period of time, typically from about zero hours, the time of administration, to about 4 hours to 20 hours or more, often for 4 hours to 16 hours, and more usually for a time period of 4 hours to 10 hours. At the end of a prolonged period of uniform release, the rate of release of drug from the dosage form may decline somewhat over a period of time, such as several hours. The dosage forms provide therapeutically effective amounts of drug for a broad range of applications and individual subject needs. The results of the release of progesterone from a representative, continuous release dosage form of this invention is provided in FIG. 5. As can be seen therefrom, progesterone is released over a period of time extending up to about 15 hours. In FIG. 5, the filled circles represent a drug granulation that does not contain any PVP (polyvinylpyrollidone), the empty triangles represent a drug granulation containing 10% PVP, and the filled squares and filled diamonds represent drug granulations containing 10% maltose. In each case, the dosage forms were formed as trilayer, continuous system with (1) a mannitol layer adjacent the exit orifice that quickly dissolves in the release bath, (2) a drug layer containing progesterone dispersed in Cremophor EL/Myvacet in calcium hydrogen phosphate in a ratio of 45/55% by weight as described in greater detail in Example 1, and (3) a push layer.

The dosage forms may also provide active agent in a pulsatile release profile. With reference to FIGS. 6–10, varying delays in the onset of the release of active agent are illustrated with formulation prepared from calcium hydrogen phosphate particles. Those results are achieved with the dosage forms described in Examples 2–6, respectively.

Figure 13:
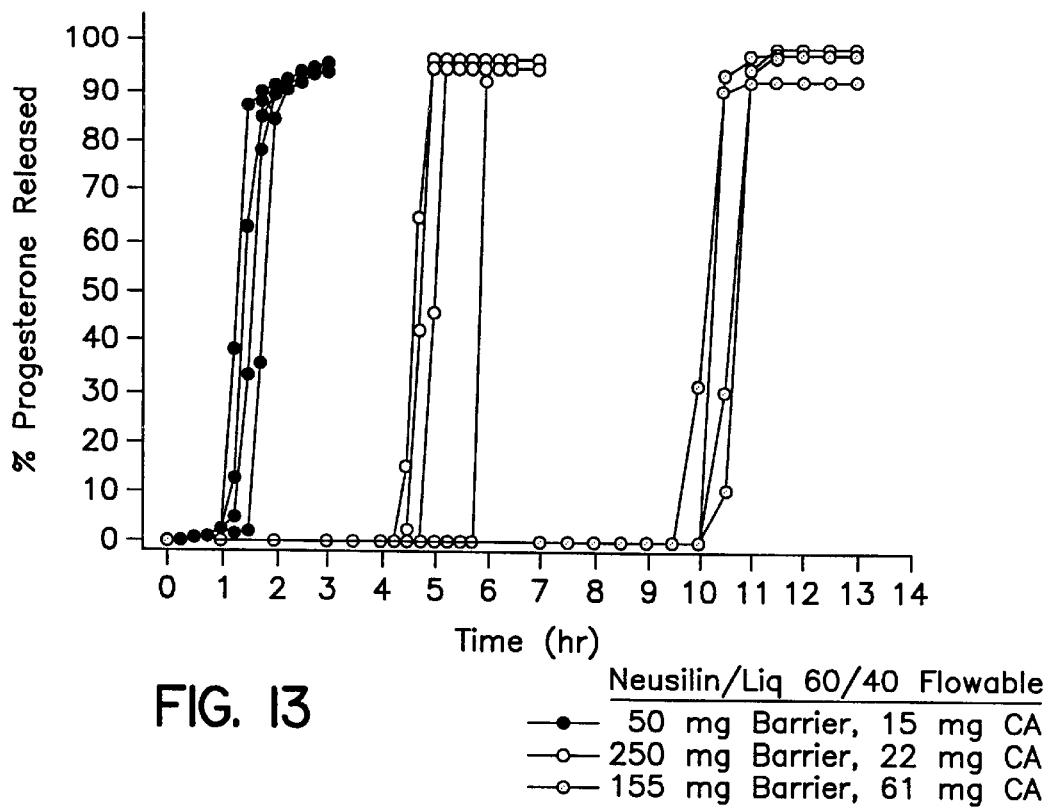
FIG. 13 presents release rate profiles of several pulse dosage forms having different periods of delay prepared with magnesium aluminometasilicate powders as described in Example 7.
Figure 14:
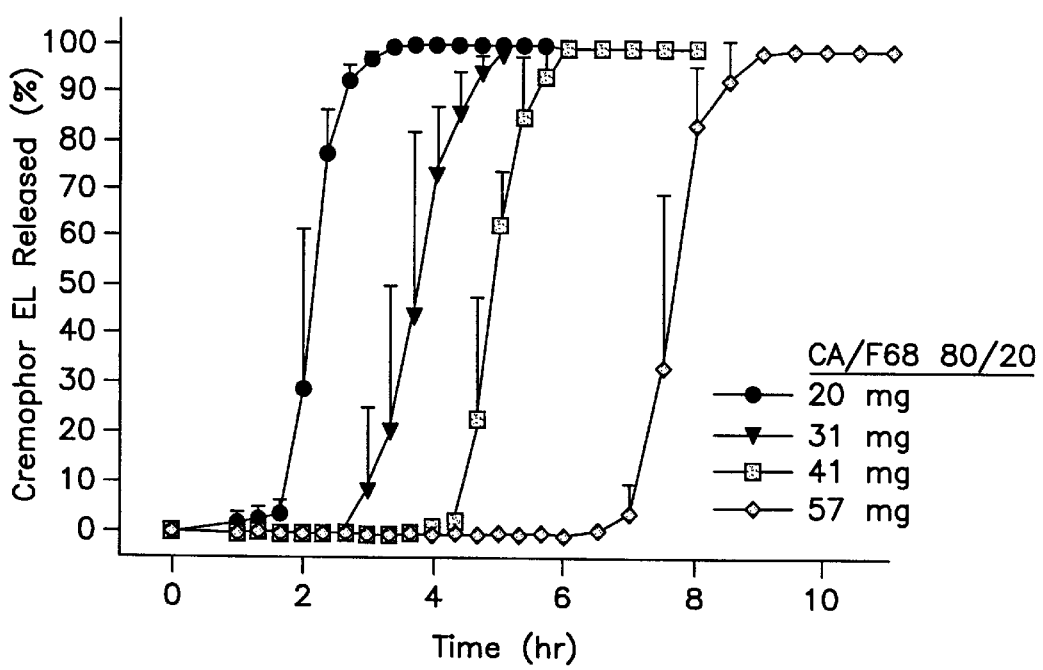
FIG. 14 presents release rate profiles of several pulse dosage forms prepared with automatic tableting equipment and illustrating the effect of membrane weight on the delay period as described in Example 8.

Results for representative formulations prepared from magnesium aluminometasilicate particles as prepared in Examples 7 and 8 are illustrated in FIGS. 13 and 14. By varying the volume or weight of the placebo layer and/or the weight of the semipermeable membrane, it is possible to control the initial period before active agent is released from the dosage form. For pulse formulations, the drug layer may be formed as a rapid release layer in which the carrier in the drug layer is eliminated or is minimally present so as to allow for rapid release of the drug particles and the liquid, active agent formulation to the environment of use. The use of a disintegrant or other agent to facilitate break-up of the porous particles may be utilized. For sustained release formulations, the general considerations surrounding the selection of parameters of the push layer, the placebo layer and the semipermeable membrane to provide a desired period of delay prior to onset of delivery of the active agent will be similar as with the pulse formulation. However, as described herein, a carrier, such as a bioerodible hydrophilic polymer or the like, may generally be utilized in greater amount to provide for continuous release of the porous particles and active agent over time.

With zero order release, upon initial administration, the dosage forms may provide a drug concentration in the plasma of the subject that increases over an initial period of time, typically several hours or less, and then provide a relatively constant concentration of drug in the plasma over a prolonged period of time, typically 4 hours to 24 hours or more. The release profiles of the dosage forms of this invention provide release of drug over the entire 24-hour period corresponding to once-a-day administration, such that steady state concentration of drug in blood plasma of a subject may be maintained at therapeutically effective levels over a 24 hour period after administration the sustained release dosage form. Steady state plasma levels of drug may typically be achieved after twenty-four hours or, in some cases, several days, e.g., 2–5 days, in most subjects.

Continuous or sustained release dosage forms of this invention release drug at a uniform rate of release over a prolonged period of time as determined in a standard release rate assay such as that described herein. When administered to a subject, the dosage forms of the invention provide blood plasma levels of drug in the subject that are less variable over a prolonged period of time than those obtained with immediate release dosage forms. When the dosage forms of this invention are administered on a regular, once-a-day basis, the dosage forms of the invention provide steady state plasma levels of drug such that the difference between $C_{max}$ and $C_{min}$ over the 24-hour period is substantially reduced over that obtained from administration of an immediate release product that is intended to release the same amount of drug in the 24-hour period as is provided from the dosage forms of the invention.

The dosage forms of this invention may be adapted to release active agent at a uniform rate of release rate over a prolonged period of time, preferably 4–6 hours or more. Measurements of release rate are typically made in vitro, in acidified water, simulated gastric fluid or simulated intestinal fluid to provide a simulation of conditions in specific biological locations, and are made over finite, incremental time periods to provide an approximation of instantaneous release rate. Information of such in vitro release rates with respect to a particular dosage form may be used to assist in selection of dosage form that will provide desired in vivo results. Such results may be determined by present methods, such as blood plasma assays and clinical observation, utilized by practitioners for prescribing available immediate release dosage forms.

Dosage forms of the present invention having zero order release rate profiles as described herein may provide to a patient a substantially constant blood plasma concentration and a sustained therapeutic effect of active agent, after administration of the dosage form, over a prolonged period of time. The sustained release dosage forms of this invention demonstrate less variability in drug plasma concentration over a 24-hour period than do immediate release formulations, which characteristically create significant peaks in drug concentration shortly or soon after administration to the subject.

The dosage forms of the invention may have a delayed onset of action incorporated directly into the dosage form by means of the placebo layer that has been described. For particular applications, it may be desirable to deliver a plurality of the dosage forms, with or without a placebo layer or other drug layer design, at a single location in the gastrointestinal tract. This may effected conveniently by combining the dosage forms of the invention with associated technology, such as for example, the Chronset® drug delivery system of Alza Corporation, Palo Alto, Calif. Such systems can be programmed to release the dosage forms at designated times and at targeted absorption sites. That technology is described in U.S. Pat. Nos. 5,110,597; 5,223,265; 5,312,390; 5,443,459; 5,417,682; 5,498,255; 5,531,736; and 5,800,422, which are incorporated herein by reference. The composite delivery system may be manufactured by loading the osmotic dosage forms described herein into the Chronset® systems, and provide for the controlled release of active agent in a variety of formats.

An illustrative general method of manufacturing dosage forms of the invention is described below in the PREPARATION. Percentages are percentages by weight unless noted otherwise. Variations in the methods and substitution of materials may be made and will be apparent from the earlier description. Equivalent or proportional amounts of such materials may be substituted for those used in the PREPARATION below. More specific descriptions are provided in the Examples and alternative materials and procedures are illustrated therein.

PREPARATION

Preparation of the Drug Layer:

A binder solution is prepared by adding hydroxypropyl cellulose (Klucel MF, Aqualon Company), "HPC", to water to form a solution containing 5 mg of HPC per 0.995 grams of water. The solution is mixed until the hydroxypropyl cellulose is dissolved. For a particular batch size, a fluid bed granulator ("FBG") bowl is charged with the required amounts of liquid, active agent formulation and the corresponding amount of porous particles, such as exemplified by the calcium hydrogen phosphate particles sold under the trademark FujiCalin. After the liquid is absorbed by the particles, the blend is mixed with, polyethylene oxide (MW 200,000) (Polyox® N-80, Union Carbide Corporation) (20.3%), hydroxypropyl cellulose (Klucel MF) (5%), polyoxyl 40 stearate (3%) and crospovidone (2%). After mixing the semi-dry materials in the bowl, the binder solution prepared as above is added. Then the granulation is dried in the FBG to a dough-like consistency suitable for milling, and the granulation is milled through a 7 or a 10 mesh screen.

The granulation is transferred to a tote blender or a V-blender. The required amounts of antioxidant, butylated hydroxytoluene ("BHT") (0.01%), and lubricant, stearic acid (1%), are sized through a 40 mesh screen and both are blended into the granulation using the tote or V-blender until uniformly dispersed (about 1 minute of blending for stearic acid and about 10 minutes of blending for BHT.

Preparation of the Osmotic Push Layer Granulation:

A binder solution is prepared by adding hydroxypropyl methylcellulose 2910 ("HPMC") to water in a ratio of 5 mg of HPMC to 1 g of water. The solution is mixed until the HPMC is dissolved. Sodium chloride powder (30%) and red ferric oxide (1.0%) are milled and screened. A fluid bed granulator ("FBG") bowl is charged with the required amounts of polyethylene oxide (MW 7,000,000) (Polyox® 303) (63.7%), HPMC (5.0%), the sodium chloride and the red ferric oxide. After mixing the dry materials in the bowl, the binder solution prepared above is added. The granulation is dried in the FBG until the target moisture content (<1% by weight water) is reached. The granulation is milled through a 7 mesh screen and transferred to a tote blender or a V-blender. The required amount of antioxidant, butylated hydroxytoluene (0.08%), is sized through a 60 mesh screen. The required amount of lubricant, stearic acid (0.25%), is sized through a 40 mesh screen and both materials are blended into the granulation using the tote or V-blender until uniformly dispersed (about 1 minute for stearic acid and about 10 minutes for BHT).

Bilayer Core Compression:

A longitudinal tablet press (Korsch press) is set up with round, deep concave punches and dies. Two feed hoppers are placed on the press. The drug layer prepared as above is placed in one of the hoppers while the osmotic push layer prepared as above is placed in the remaining hopper.

The initial adjustment of the tableting parameters (drug layer) is performed to produce cores with a uniform target drug layer weight. The second layer adjustment (osmotic push layer) of the tableting parameters is performed which bonds the drug layer to the osmotic layer to produce cores with a uniform final core weight, thickness, hardness, and friability. The foregoing parameters can be adjusted by varying the fill space and/or the force setting. A typical tablet containing a target amount of drug may be approximately 0.465 inches long and approximately 0.188 inches in diameter.

Preparation of the Subcoat Solution and Subcoated System:

The subcoat solution is prepared in a covered stainless steel vessel. The appropriate amounts of povidone (K29–32) (2.4%) and hydroxypropyl cellulose (MW 80,000) (Klucel EF, Aqualon Company) (5.6%) are mixed into anhydrous ethyl alcohol (92%) until the resulting solution is clear. The bilayer cores prepared above are placed into a rotating, perforated pan coating unit. The coater is started and after the coating temperature of 28–36° C. is attained, the subcoating solution prepared above is uniformly applied to the rotating tablet bed. When a sufficient amount of solution has been applied to provide the desired subcoat weight gain, the subcoat process is stopped. The desired subcoat weight will be selected to provide acceptable residuals of drug remaining in the dosage form as determined in the release rate assay for a 24-hour period. Generally, it is desirable to have less than 10%, more preferably less than 5%, and most preferably less than 3% of residual drug remaining after 24 hours of testing in a standard release rate assay as described herein, based on the initial drug loading. This may be determined from the correlation between subcoat weight and the residual drug for a number of dosage forms having the same bilayer core but different subcoat weights in the standard release rate assay.

Preparation of the Rate Controlling Membrane and Membrane Coated System:

Subcoated bilayer cores prepared as above are placed into a rotating, perforated pan coating unit. The coater is started, and after the coating temperature (28–38° C.) is attained, a coating solution such as illustrated in A, B or C below is uniformly applied to the rotating tablet bed until the desired membrane weight gain is obtained. At regular intervals throughout the coating process, the weight gain is determined and sample membrane coated units may be tested in the release rate assay to determine a $T_{90}$ go for the coated units. Weight gain may be correlated with $T_{90}$ for membranes of varying thickness in the release rate assay. When sufficient amount of solution has been applied, conveniently determined by attainment of the desired membrane weight gain for a desired $T_{90}$, the membrane coating process is stopped.

Illustrative Rate Controlling Membrane Compositions:

A coating solution is prepared in a covered stainless steel vessel. The appropriate amounts of acetone (5650 g) and water (297 g) are mixed with the poloxamer 188 (16 g) and cellulose acetate (297 g) until the solids are completely dissolved. The coating solution has about 5% solids upon application.

Acetone (5054 g) is mixed with cellulose acetate (277.2 g) until the cellulose acetate is completely dissolved. Polyethylene glycol 3350 (2.8 g) and water (266 g) are mixed in separate container. The two solutions are mixed together until the resulting solution is clear. The coating solution has about 5% solids upon application.

Acetone (7762 g) is mixed with cellulose acetate (425.7 g) until the cellulose acetate is completely dissolved. Polyethylene glycol 3350 (4.3 g) and water (409 g) are mixed in separate container. The two solutions are mixed together until the resulting solution is clear. The coating solution has about 5% solids upon application.

Drilling of Membrane Coated Systems:

One exit port is drilled into the drug layer end of the membrane coated system. During the drilling process, samples are checked at regular intervals for orifice size, location, and number of exit ports.

Drying of Drilled Coated Systems:

Drilled coated systems prepared as above are placed on perforated oven trays which are placed on a rack in a relative humidity oven at 40° C. (43–45% relative humidity) and dried to remove the remaining solvents from the coating layers.

Color and Clear Overcoats:

Optional color or clear coats solutions are prepared in a covered stainless steel vessel. For the color coat 88 parts of purified water is mixed with 12 parts of Opadry II [color not critical] until the solution is homogeneous. For the clear coat 90 parts of purified water is mixed with 10 parts of Opadry Clear until the solution is homogeneous. The dried cores prepared as above are placed into a rotating, perforated pan coating unit. The coater is started and after the coating temperature is attained (35–45° C.), the color coat solution is uniformly applied to the rotating tablet bed. When sufficient amount of the dispersion has been applied, as conveniently determined when the desired color overcoat weight gain has been achieved, the color coat process is stopped. Next, the clear coat solution is uniformly applied to the rotating tablet bed. When sufficient amount of solution has been applied, or the desired clear coat weight gain has been achieved, the clear coat process is stopped. A flow agent (e.g., Car-nu-bo wax) is applied to the tablet bed after clear coat application.

Variations in the foregoing procedure will be apparent to one skilled in the art. The examples are provided to illustrate representative dosage forms of the invention prepared by analogous methods.

ASSAY

The release rate of drug from devices containing the dosage forms of the invention may be determined in standardized assays such as the following. The method involves releasing systems into a release liquid medium, such as acidified water (pH 3), artificial gastric fluid or artificial intestinal fluid. Aliquots of sample release rate solutions are injected onto a chromatographic system to quantify the amount of drug released during specified test intervals. Drug is resolved on a $C_{18}$ column and detected by UV absorption at the appropriate wavelength for the drug in question. Quantitation is performed by linear regression analysis of peak areas from a standard curve containing at least five standard points.

Samples are prepared with the use of a USP Type 7 Interval Release Apparatus. Each system (invention device) to be tested is weighed. Then, each system is glued to a plastic rod having a sharpened end, and each rod is attached to a release rate dipper arm. Each release rate dipper arm is affixed to an up/down reciprocating shaker (USP Type 7 Interval Release Apparatus), operating at an amplitude of about 3 cm and 2 to 4 seconds per cycle. The rod ends with the attached systems are continually immersed in 50 ml calibrated test tubes containing 50 ml of the release medium, equilibrated in a constant temperature water bath controlled at 37° C.±0.5° C. At the end of each time interval specified, typically one hour or two hours, the systems are transferred to the next row of test tubes containing fresh release medium. The process is repeated for the desired number of intervals until release is complete. Then the solution tubes containing released drug are removed and allowed to cool to room temperature. After cooling, each tube is filled to the 50 ml mark, each of the solutions is mixed thoroughly, and then transferred to sample vials for analysis by high pressure liquid chromatography ("HPLC"). Standard solutions of drug are prepared in concentration increments encompassing the range of 5 micrograms to about 400 micrograms and analyzed by HPLC. A standard concentration curve is constructed using linear regression analysis. Samples of drug obtained from the release test are analyzed by HPLC and concentration of drug is determined by linear regression analysis. The amount of drug released in each release interval is calculated. Alternatively, concentration of drug may be determined by uv analysis.

EXAMPLE 1

A delivery system (FIG. 3) is manufactured for dispensing a beneficial drug progesterone in a controlled manner over a prolonged period of time. A self-emulsifying drug solution comprising, in weight percent, 2% progesterone, 49% polyoxyl 35 castor oil (Cremophor EL, BASF Corporation) and 49% distilled acetylated monoglyceride (Myvacet 9-45) is prepared. Then, 38% of the solution is blended with 47% of porous calcium hydrogen phosphate (FujiCalin SG) in a mixing vessel. Four percent of hydroxypropyl methylcellulose (HPMC E5) dissolved in ethanol is slowly added into the mixing vessel containing the blend, and is mixed with the blend until even consistency of wet mass is attained. The wet mass is passed through a screen and then dried at ambient conditions overnight. The mass is rescreened, and then 10% of maltose and 1% magnesium stearate is added to the granules and blended.

Next, an osmotic-layer forming composition comprising, in weight percent, 58.75% sodium carboxymethyl cellulose (7H4F), 30.0% sodium chloride, 5.0% hydroxypropyl methylcellulose (E5), 1.0% red ferric oxide is prepared by passing each component a 40-mesh stainless steel screen and then blending in a Galtt fluid-bed granulator and sprayed with 5.0% hydroxypropyl cellulose (EF) solution in purified water until homogeneous granules form. These granules are passed through an 8-mesh stainless steel screen and mixed with 0.25% magnesium stearate.

376 Mg of the drug-layer granules and 169 mg of the osmotic(push)-layer granules are compressed into bi-layer longitudinal caplets using 0.265" round punch and Carver press. Prior to compression, a small amount of mannitol is placed on the drug layer composition to facilitate ejection of the tablets from the tooling. The tablets are coated with a subcoat composition comprising 5% of Klucel JF and 95% of ethanol using a Freud Hi-coater. The weight of the subcoat is about 3 mg. Then, the subcoated tablets are coated with a rate-controlling membrane composition. The membrane-forming composition comprises, in weight percent, 85% cellulose acetate having an acetyl content of 39.8% and 15% Pluronic F68. The membrane-forming composition is dissolved in acetone to make a 5% solid solution. The membrane-forming composition is sprayed onto the tablets in a Freud Hi-coater. The membrane weight is about 22 mg. Finally, an exit orifice (230 mil) is cut mechanically on the drug-layer side of the system. The final system delivers progesterone in-vitro with a zero order delivery as shown in FIG. 5.

EXAMPLE 2

A delivery system (FIG. 4) is manufactured for dispensing a beneficial drug progesterone as a delayed pulse. First, a self-emulsifying drug solution comprising, in weight percent, 2% progesterone, 49% Cremophor EL and 49% Myvacet 9-45 is prepared. Then, 38% of the solution is blended with 47% of porous calcium hydrogen phosphate (FujiCalin SG) in a mixing vessel. Four percent of HPMC E5 dissolved in ethanol is slowly added into the mixing vessel containing the blend, and is mixed with the blend until even consistency of wet mass is attained. The wet mass is passed through a screen and then dried at ambient conditions until the granulation reaches the specified moisture level. The mass is rescreened, and then 10% of maltose and 1% magnesium stearate is added to the granules and blended.

Next, an osmotic (push)-layer forming composition comprising, in weight percent, 58.75% sodium carboxymethyl cellulose (7H4F), 30.0% sodium chloride, 5.0% hydroxypropyl methylcellulose (E5), 1.0% red ferric oxide is prepared by passing each component a 40-mesh stainless steel screen and then blending in a Galtt fluid-bed granulator and sprayed with 5.0% hydroxypropyl cellulose (EF) solution in purified water until homogeneous granules form. These granules are passed through an 8-mesh stainless steel screen and mixed with 0.25% magnesium stearate.

Figure 6:
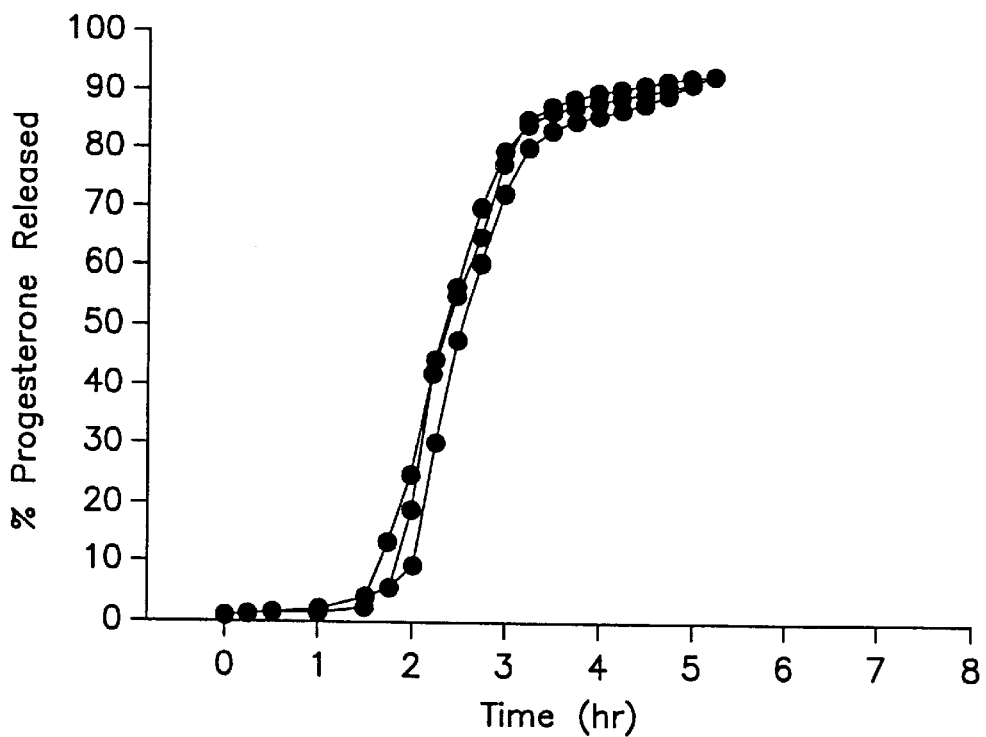
FIGS. 6–10 illustrate the release profile (percent of active agent released as a function of time) of the active agent progesterone for representative dosage forms of the invention having a delayed pulse release, wherein the initial delay is 2 hours, 3 hours, 4–5 hours, 6–7 hours and about 10 hours for the dosage forms described in Examples 2, 3, 4, 5 and 6, respectively.

Then, 50 mg of placebo-layer granules (having the same composition as the osmotic-layer), 195 mg of the drug-layer granules and 165 mg of the osmotic-layer granules are compressed into tri-layer longitudinal caplets using 0.265" round punch and Carver press. The tablets are coated with a subcoat composition comprising 5% of Klucel JF and 95% of ethanol using a Freud Hi-coater. The weight of the subcoat is about 3 mg. Then, the subcoated tablets are coated with a rate-controlling membrane composition. The membrane-forming composition comprises, in weight percent, 85% cellulose acetate having an acetyl content of 39.8% and 15% Pluronic F68. The membrane-forming composition is dissolved in acetone to make a 5% solid solution. The membrane-forming composition is sprayed onto the tablets in a Freud Hi-coater. The membrane weight is about 22 mg. Finally, an exit orifice (230 mil) is cut mechanically on the 1 st placebo-layer side of the system. The final system delivers progesterone in-vitro with a 2 hour delayed pulse as shown in FIG. 6.

EXAMPLE 3

Figure 7:
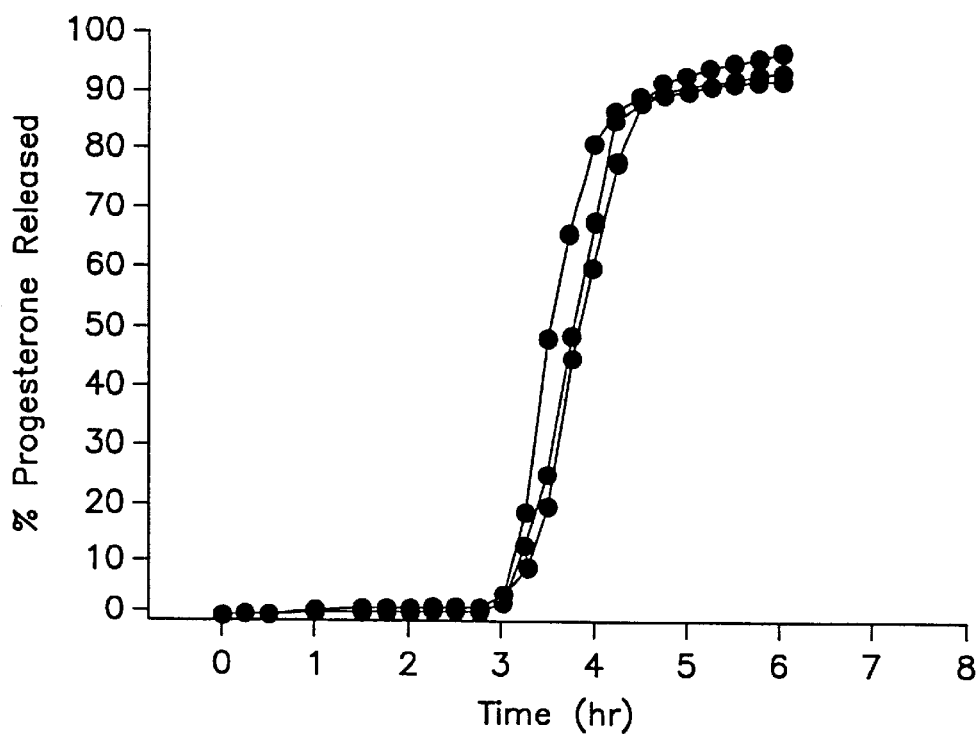

The procedure of Example 2 is repeated in this example for providing the following dosage form:

A dosage form composed of the drug-layer, osmotic-layer and the membrane, the compositions of which are all identical to those in Example 2 is prepared, except that the placebo-layer weight is 100 mg. The final dosage form delivers progesterone in-vitro with a 3 hour delayed pulse as shown in FIG. 7.

EXAMPLE 4

Figure 8:
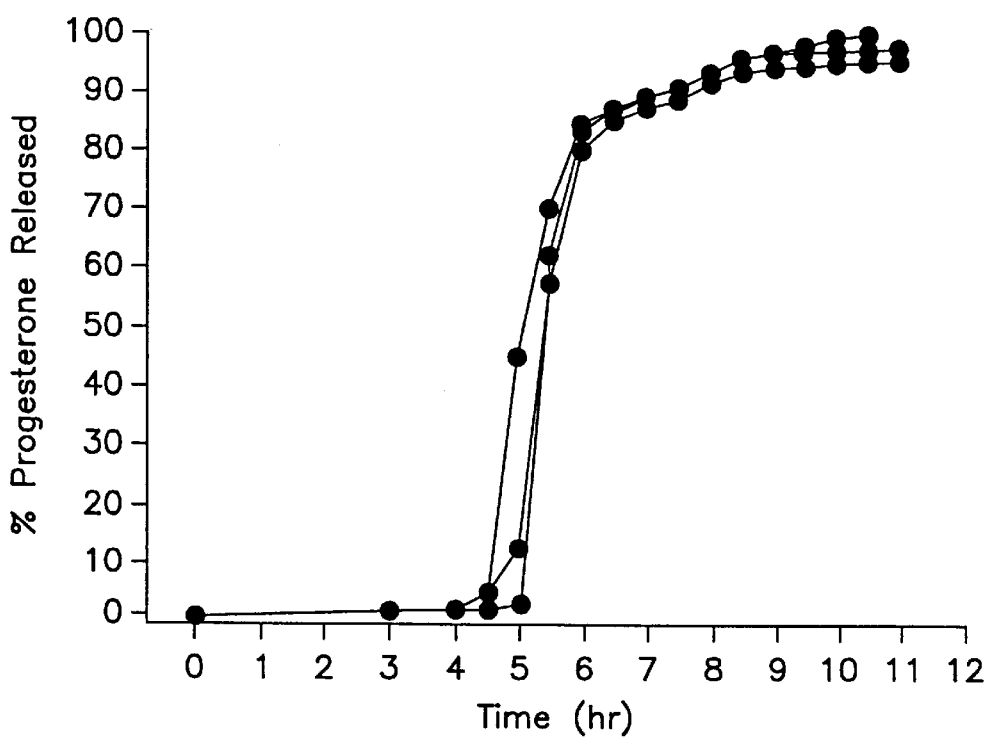

The procedure of Example 2 is repeated in this example for providing the following dosage form:

A dosage form composed of the drug-layer, osmotic-layer and the membrane, the compositions of which are all identical to those in Example 2 is prepared, except that the placebo-layer weight is 155 mg. The final dosage form delivers progesterone in-vitro with a 5 hour delayed pulse as shown in FIG. 8.

EXAMPLE 5

Figure 9:
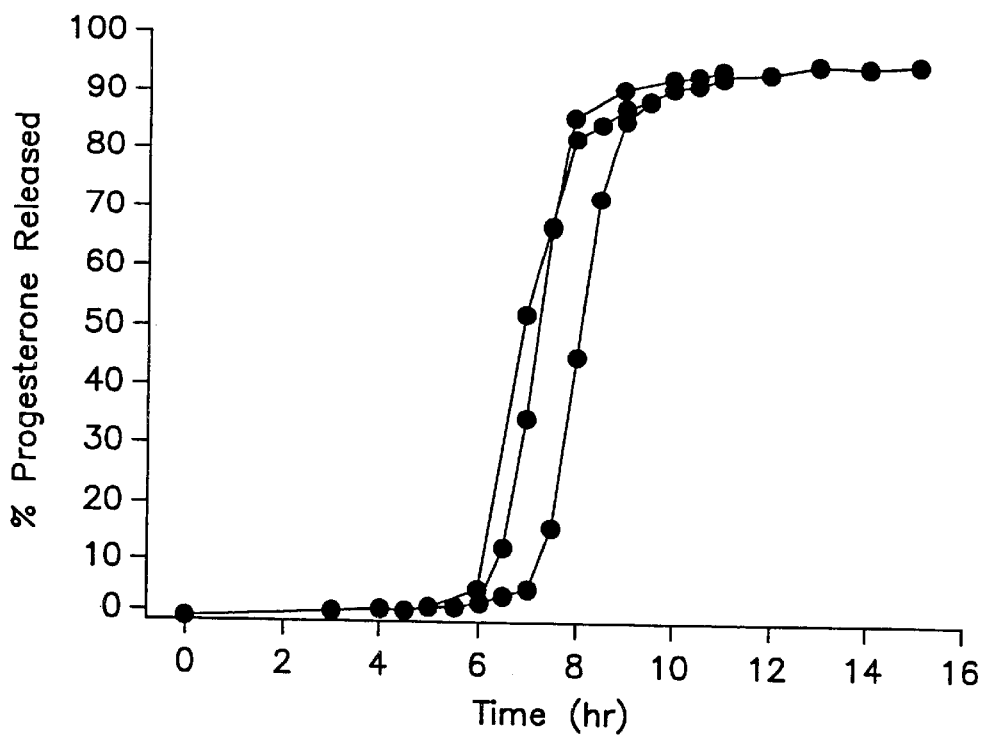

The procedure of Example 2 is repeated in this example for providing the following dosage form:

A dosage form composed of the drug-layer, osmotic-layer and the membrane, the compositions of which are all identical to those in Example 2 is prepared, except that the placebo-layer weight is 250 mg. The final dosage form delivers progesterone in-vitro with a 6–7 hour delayed pulse as shown in FIG. 9.

EXAMPLE 6

Figure 10:
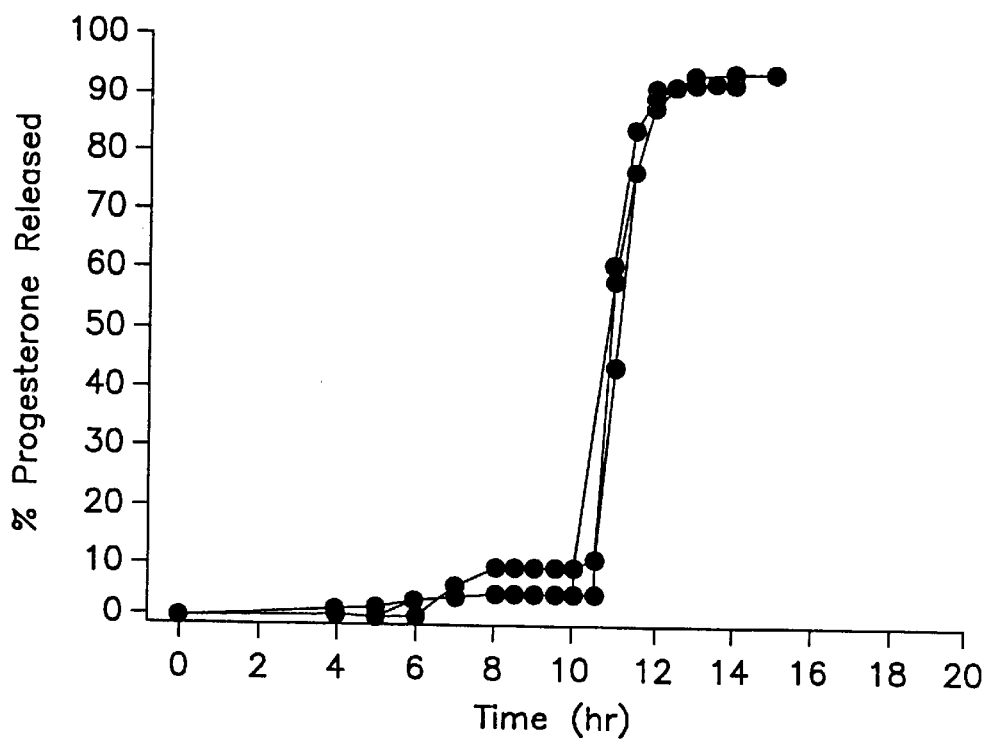

The procedure of Example 2 is repeated in this example for providing the following dosage form:

A dosage form composed of the osmotic-layer and the membrane layer compositions which are identical to those in Example 2 is prepared, except that the placebo-layer weight is 155 mg, the drug-layer granulation is composed of 36% of the drug solution described in Example 2, 44% calcium phosphate, 4% HPMC E5, 1% Mg stearate and 15% maltose, and the weight of the rate-controlling membrane is 105 mg. The final dosage form delivers progesterone in-vitro with a 10-h delayed pulse as shown in FIG. 10.

EXAMPLE 7

The following formulations are prepared for incorporation into the dosage forms illustrated in FIG. 3 and FIG. 4 in accordance with the general procedures described. All percentages are by weight unless otherwise noted. The Polyox 303 push layer is used as the barrier or delay layer (sometimes denoted as a placebo layer) for those dosage forms illustrated in FIG. 4 and as the expandable or push layer in both dosage forms illustrated in FIGS. 3 and 4. Tableting is done on a Carver press at a force of one-quarter ton.

| Polyox 303 push and delay layer formulation | |
|---|---|
| Polyox 303 | 63.68% |
| Sodium Chloride | 30% |
| HPMC E5 | 5% |
| Red Ferric Oxide | 1% |
| Mg Stearate | 0.25% |
| BHT | 0.08% |

Polyox 303 Preparation:
The Polyox, NaCl, and oxide are blended in a Glatt fluid-bed granulator and sprayed with a 5% HPMC E5 solution in purified water until homogeneous granules are formed. These granules are passed through a 16-mesh stainless steel screen and mixed with magnesium stearate and BHT.

| FujiCalin formulations for drug tablet dissolution | | | | | |
|---|---|---|---|---|---|
| Formulation | A | B | C | D | E |
| FujiCalin SG | 52% | 52% | 47% | 47% | 44% |
| Cremophor EL | — | 20.6% | 18.6% | 18.6% | 17.6% |
| Cremophor RH | 20.6% | — | — | — | — |
| Myvacet 9-45 | 20.6% | 20.6% | 18.6% | 18.6% | 17.6% |
| Progesterone | 0.84% | 0.84% | 0.76% | 0.76% | 0.72% |
| HPMC E5 | 4.96% | 4.96% | 4.04% | 4.04% | 4.08% |
| PVP XL | — | — | 10% | — | 15% |
| Maltose | — | — | — | 10% | — |
| Mg Stearate | 1% | 1% | 1% | 1% | 1% |

Fujicalin Tablet Preparation:
The progesterone, Cremophor and Myvacet are dissolved by combining the materials in a mixing bowl and mixing with a magnetic stir bar in a 40C water bath for 3 hours. The resulting solution is slowly added to the FujiCalin granules in a mechanical mixing bowl (KitchenAid mixer) while mixing. Mixing is continued for 10 minutes and the HPMC E5, wet granulated with ethanol, is added. The resulting mass is passed through a 20-mesh screen and allowed to dry overnight under ambient conditions. The dried material is again screened through a 20-mesh screen, and the dried granules are blended with the PVP XL on a roller mixer for 10 minutes. Then, the magnesium stearate is added, and the mixture is blended on the roller mixer for an additional 2 minutes. The resulting material is suitable for tableting. To facilitate release of the tablets from the die components, a small amount of mannitol may be applied to the outside surface of the drug formulation being tableted. Tableting is done on a Carver press at a force of one-quarter ton.

Figure 11:
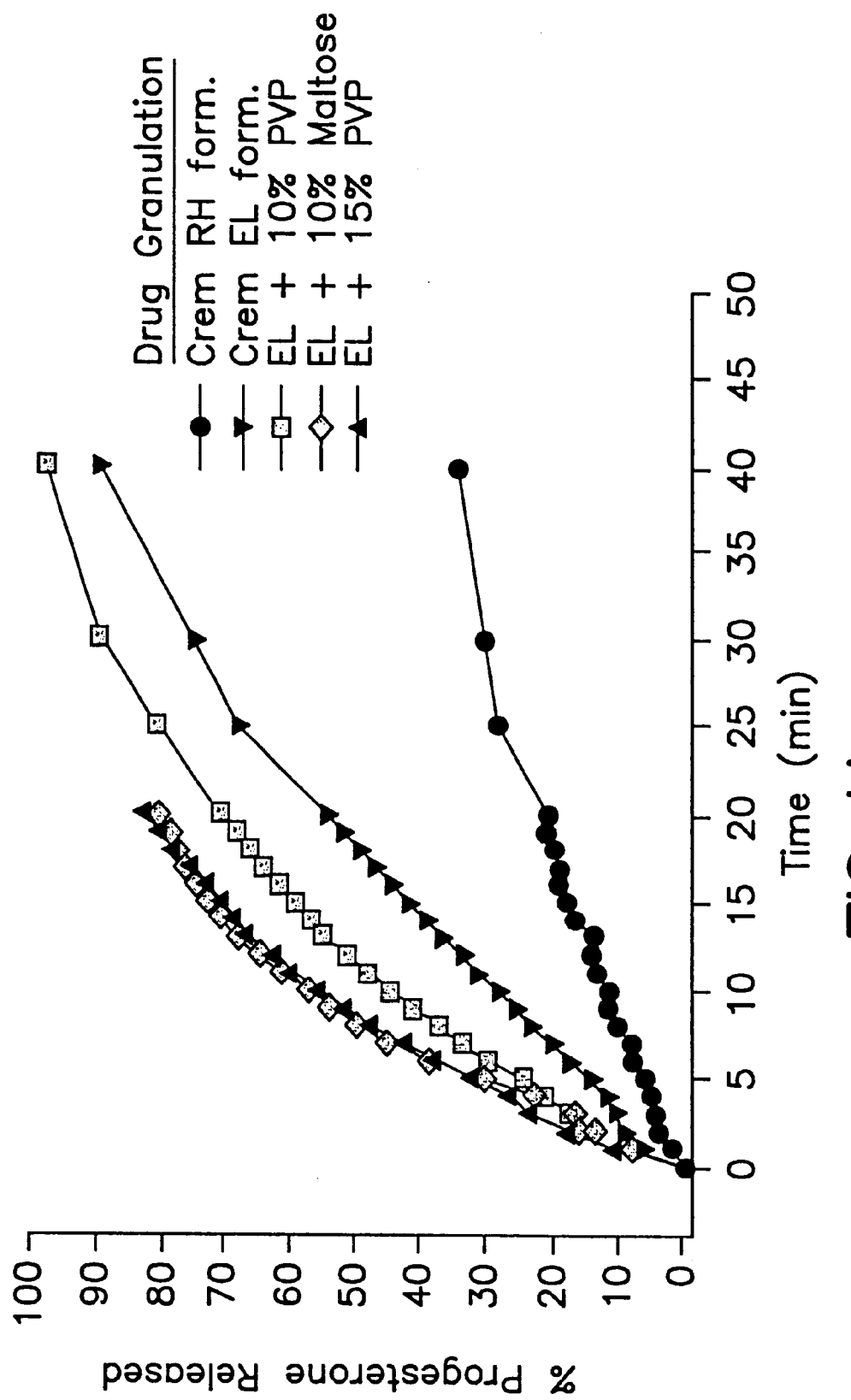
FIG. 11 presents the dissolution profiles in artificial gastric fluid of several different drug layer formulations prepared with calcium hydrogen phosphate as described in Example 7.

The dissolution profiles for tablets containing the various drug formulations described above in artificial gastric fluid developed in a USP bath are represented in FIG. 11, in which circles represent the formulation A, inverted triangles represent formulation B, squares represent formulation C, diamonds represent formulation D, and triangles represent formulation F.

Pulse System Tableting:
Tri-layer tablets containing the foregoing formulations and completed dosage forms are prepared according to the general procedures described in Example 1. The dosage forms provide pulsed delivery of progesterone having varying delay periods depending on the amount of the material in the placebo/barrier layer.

Neusilin formulations for drug tablet

| Formulation | G/K | H/L | I/M | J |
|---|---|---|---|---|
| Neusilin US2 | 34% | 36% | 38% | 40% |
| Cremophor EL | 24.99% | 26.46% | 27.93% | 29.4% |
| Myvacet 9-45 | 24.99% | 26.46% | 27.93% | 29.4% |
| Progesterone | 1.02% | 1.08% | 1.14% | 1.2% |
| Ac-Di-Sol or PVP XL | 15% | 10% | 5% | 0% |

Figure 12:
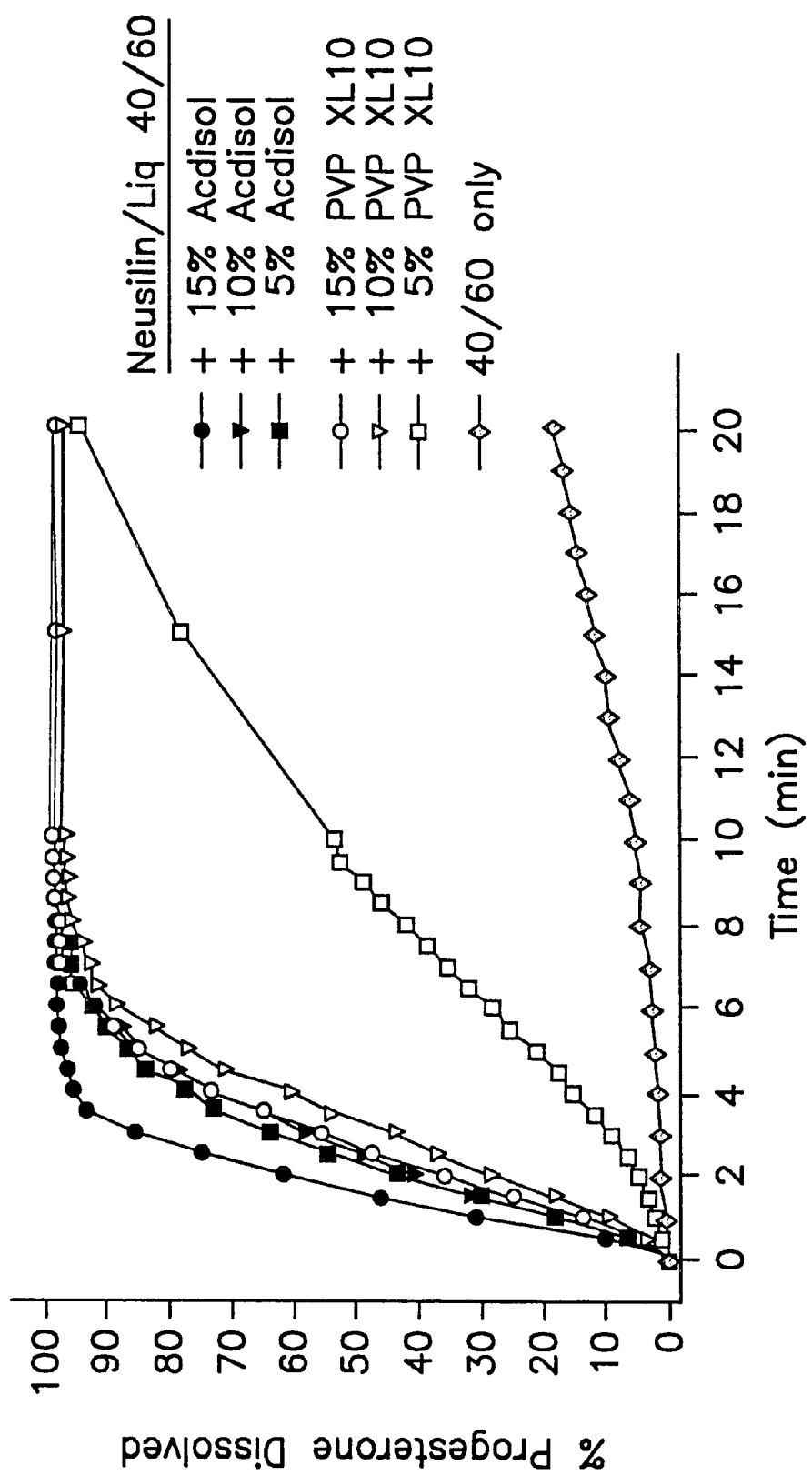
FIG. 12 presents the dissolution profiles in artificial intestinal fluid of several different drug layer formulations prepared with magnesium aluminometasilicate powders as described in Example 7.

Neusilin Tablet Preparation:

Neusilin tablets having formulations as set forth above are prepared in a similar manner to that described for FujiCalin above except that the magnesium stearate and its mixing step are eliminated. Formulations G, H, and I are formed with Ac-Di-Sol. Formulations K, L, and M are formed with PVP XL. Tableting is done on a Carver press at a force of one-quarter ton. Tablets are readily ejected from the die without the use of mannitol. The dissolution profiles for the various formulations are represented in FIG. 12. The filled circles represent formulation G, filled, inverted triangles represent formulation H, and filled squares represent formulation I. The open circles represent formulation K, open, inverted triangles represent formulation L, and open squares represent formulation M. The filled diamonds represent formulation J.

Pulse System Tableting:

Tri-layer tablets are prepared by the general procedures described in Example 1, and coated with a semipermeable membrane of cellulose acetate/Pluronics F68 at a weight ratio of 85/15 as described. Representative release profiles for the tri-layer, pulse dosage forms are illustrated in FIG. 13 for formulations as described above with 5% Acdisol, and barrier/membrane layer weights of 50/15 mg, 250/22 mg, and 155/61 mg, providing delay periods of about 1, 5 and 10 hours, respectively.

EXAMPLE 8

This example illustrates that the dosage forms may be tableted with conventional, automatic tableting equipment. Active agent was omitted from the liquid formulation sorbed into the porous particles because of limitations on the use of drug with equipment that was being used in on-going operations. Since Cremophor EL could be assayed, it served the dual role of liquid formulation sorbed into particles and entity for determination of release from sample dosage forms. The particle formulation, without drug, is prepared as a 10 kg batch for use in a trilayer dosage form as illustrated in FIG. 4. The trilayer tablets are formed on a multi-station trilayer tablet press having 11 stations. The press is operated at 5 rpm and the compression forces utilized for the first layer (osmotic push layer), second layer (placebo/particles) and third layer (barrier) are 100, 100, and 4,000 N, respectively. The weights in each tablet of the osmotic/placebo (particles)/barrier layers are 175/160/125 mg, respectively. Tablets prepared are expelled from the tableting cavity without sticking to the cavity walls or the punch.

The following formulation was utilized for the preparation of the mock-drug layer:

| | |
|---|---|
| Neusilin US2 | 55.8% |
| Cremophor EL | 18.6% |
| Myvacet 9-45 | 18.6% |
| Ac-Di-Sol | 4.5% |
| Stearic Acid | 2.0% |
| Mg Stearate | 0.5% |

Particle Layer Preparation:

The Cremophor and Myvacet are mixed in a large stainless steel pot with a mechanical mixer for 20 minutes. In a large Hobart mixer Neuslin powder is added to the bowl, and the Cremophor/Myvacet blend is slowly added through a funnel to the powder over a 5 minute period while stirring is maintained. Material on the sides of the bowl is scraped down and the blend is mixed for 2 minutes more. Then the material is transferred to a Gemco V-blender, and the Ac-Di-Sol and stearic acid are added. The resulting mass is mixed for 5 minutes, after which the magnesium stearate is added and the mass mixed for 1 minute more. The blended material flows easily and is may be directly loaded into the hoppers of the tableting press.

Tri-layer tablets prepared from the above formulation as the (drug)/particle layer and the Polyox formulation for the barrier and push layers described above were prepared as described with semipermeable membrane coats formed from 80/20 cellulose acetate/Pluronics F68 of 20 mg, 31 mg, 41 mg and 57 mg and a 190 mil exit orifice. The release profiles (measured in terms of Cremophor released since no drug was present) of those systems are presented in FIG. 14. The filled circles correspond to a 20 mg membrane coat, filled, inverted triangles correspond to a 31 mg membrane coat, filled squares correspond to a 41 mg membrane coat, and filled diamonds correspond to a 57 mg membrane coat.

The present invention is described and characterized by one or more of the following technical features and/or characteristics, either alone or in combination with one or more of the other features and characteristics: a dosage form for an active agent comprising a wall defining a cavity, the wall having an exit orifice formed or formable therein and at least a portion of the wall being semipermeable; an expandable layer located within the cavity remote from the exit orifice and in fluid communication with the semipermeable portion of the wall; a drug layer located within the cavity adjacent the exit orifice and in direct or indirect contacting relationship with the expandable layer; the drug layer comprising a liquid, active agent formulation absorbed in porous particles, the porous particles being adapted to resist compaction forces sufficient to form a compacted drug layer without significant exudation of the liquid, active agent formulation, the dosage form optionally having a placebo layer between the exit orifice and the drug layer; a dosage form comprising a flow-promoting layer interposed between the inner surface of the wall and at least the external surface of the drug layer located within the cavity; a dosage form for an active agent comprising a wall defining a cavity, the wall having an exit orifice formed or formable therein and at least a portion of the wall being semipermeable; an expandable layer located within the cavity remote from the exit orifice and in fluid communication with the semipermeable portion of the wall; a drug layer located within the cavity adjacent the exit orifice and in direct or indirect contacting relationship with the expandable layer; the drug layer comprising a liquid, active agent formulation absorbed in porous particles, the porous particles, having a mean particle size of 50–150 microns, being formed by spray drying a scale-like calcium hydrogen phosphate with a specific surface area of 20 m²/g to 60 m²/g, an apparent specific volume of 1.5 ml/g or more, an oil absorption capacity of 0.7 ml/g or more, a primary particle size of 0.1μ to 5μ, and an average particle size of 2μ to 10μ among secondary particles that are aggregates of the primary particles, the scale-like calcium hydrogen phosphate being represented by the following general formula:

CaHPO₄.mH₂O wherein m satisfies the relationship 0≦m≦0.5 or 0≦m≦2.0, the dosage form optionally having a placebo layer between exit orifice and the drug layer; a dosage form for an active agent comprising a wall defining a cavity, the wall having an exit orifice formed or formable therein and at least a portion of the wall being semipermeable; an expandable layer located within the cavity remote from the exit orifice and in fluid communication with the semipermeable portion of the wall; a drug layer located within the cavity adjacent the exit orifice and in direct or indirect contacting relationship with the expandable layer; the drug layer comprising a liquid, active agent formulation absorbed in porous particles, the porous particles being calcium hydrogen phosphate having a specific volume of at least 1.5 ml/g, a BET specific surface area of at least 20 m²/g, and a water absorption capacity of at least 0.7 ml/g, the dosage form optionally having a placebo layer between the exit orifice and the drug layer; a dosage form for an active agent comprising a wall defining a cavity, the wall having an exit orifice formed or formable therein and at least a portion of the wall being semipermeable; an expandable layer located within the cavity remote from the exit orifice and in fluid communication with the semipermeable portion of the wall; a drug layer located within the cavity adjacent the exit orifice and in direct or indirect contacting relationship with the expandable layer; the drug layer comprising a liquid, active agent formulation absorbed in porous particles, the porous particles being calcium hydrogen phosphate having a specific volume of at least 1.5 ml/g, a BET specific area of at least 20 m²/g, and a water absorption capacity of at least 0.7 ml/g, the particles having a size distribution of 100% less than 40 mesh, 50%–100% less than 100 mesh and 10%–60% less than 200 mesh, the dosage form optionally having a placebo layer between the exit orifice and the drug layer; a dosage form for an active agent comprising a wall defining a cavity, the wall having an exit orifice formed or formable therein and at least a portion of the wall being semipermeable; an expandable layer located within the cavity remote from the exit orifice and in fluid communication with the semipermeable portion of the wall; a drug layer located within the cavity adjacent the exit orifice and in direct or indirect contacting relationship with the expandable layer; the drug layer comprising a liquid, active agent formulation absorbed in porous particles, the porous particles being calcium hydrogen phosphate having a bulk specific volume of 1.5 ml/g–5 ml/g, a BET specific area of 20 m²/g-60 m²/g, a water absorption capacity of at least 0.7 ml/g, and a mean particle size of 50 microns or greater, the dosage form optionally having a placebo layer between the exit orifice and the drug layer; a dosage form for an active agent comprising a wall defining a cavity, the wall having an exit orifice formed or formable therein and at least a portion of the wall being semipermeable; an expandable layer located within the cavity remote from the exit orifice and in fluid communication with the semipermeable portion of the wall; a drug layer located within the cavity adjacent the exit orifice and in direct or indirect contacting relationship with the expandable layer; the drug layer comprising a liquid, active agent formulation absorbed in porous particles, the porous particles being adapted to resist compaction forces sufficient to form a compacted drug layer without significant exudation of the liquid, active agent formulation, the porous particles being formed from material selected from calcium hydrogen phosphate, magnesium aluminometasilicates, microcrystalline celluloses and silicon dioxides; a dosage form comprising at least two drug layers separated by at least one inert layer; a dosage form comprising at least two drug layers, each of said drug layers containing a different active agent; a method of facilitating the release of an active agent from a dosage form comprising sorbing a liquid formulation of the active agent into a plurality of porous particles, the particles, having a mean particle size of 5–150 microns, being formed by spray drying a scale-like calcium hydrogen phosphate with a specific surface area of 20 m²/g to 60 m²/g, an apparent specific volume of 1.5 ml/g or more, an oil absorption capacity of 0.7 ml/g or more, a primary particle size of 0.1μ to 5μ, and an average particle size of 2μ to 10μ among secondary particles that are aggregates of the primary particles, the scale-like calcium hydrogen phosphate being represented by the following general formula:

CaHPO₄.mH₂O wherein m satisfies the relationship 0≦m≦0.5 or 0≦m≦2.0, and dispersing the particles throughout a bioerodible carrier; a composition comprising a liquid formulation of an active agent sorbed into a plurality of porous particles, the particles being formed by spray drying a scale-like calcium hydrogen phosphate with a specific surface area of 20 m²/g to 60 m²/g, an apparent specific volume of 1.5 ml/g or more, an oil absorption capacity of 0.7 ml/g or more, a primary particle size of 0.1μ to 5μ, and an average particle size of 2μ to 10μ among secondary particles that are aggregates of the primary particles, the scale-like calcium hydrogen phosphate being represented by the following general formula:

CaHPO₄.mH₂O wherein m satisfies the relationship 0≦m≦0.5 or 0≦m≦2.0, and dispersed throughout a bioerodible carrier, the particles being released in the environment of use over a prolonged period of time; a dosage form wherein the liquid, active agent formulation comprises a self-emulsifying formulation; a dosage form wherein the active agent has low water solubility; a dosage form wherein the liquid, active agent formulation comprises an absorption enhancer; a dosage form wherein the liquid, active agent formulation comprises at least 30% by weight of the drug layer; dosage form wherein the porous particle comprises magnesium aluminometasilicate represented by the general formula Al₂O₃MgO.2SiO₂.nH₂O wherein n satisfies the relationship 0≦n≦10; a dosage form wherein the porous particle comprises magnesium aluminometasilicate represented by the general formula Al₂O₃MgO.2SiO₂.nH₂O wherein n satisfies the relationship 0≦n≦10 and having a specific surface area of about 100–300 m²/g, an oil absorption capacity of about 1.3–3.4 ml/g, a mean particle size of about 1–2 microns, an angle of repose about 25°–45°, a speific gravity of about 2 g/ml and a specific volume of about 2.1–12 ml/g; a dosage form having placebo layer located between the drug layer and an exit orifice; a dosage form comprising a pH regulating agent selected from organic acids, inorganic acids and bases; a dosage form comprising a chelating agent.

The above-described exemplary embodiments are intended to be illustrative in all respects, rather than restrictive, of the present invention. Thus, the present invention is capable of implementation in many variations and modifications that can be derived from the description herein by a person skilled in the art. All such variations and modifications are considered to be within the scope and spirit of the present invention as defined by the following claims.

What is claimed is:

1. A dosage form comprising a semipemeable wall, an exit orifice, an expandable layer, and a compacted drug layer, wherein the semipermeable wall is positioned over the at least a portion of the expandable layer and the compacted drug layer comprises a liquid active agent formulation absorbed in porous particles, the porous particles being adapted to resist compaction forces sufficient to form a compacted drug layer such that the dosage form includes a compacted drug layer comprising at least 30% by weight of the liquid active agent formulation.

2. A dosage form of claim 1 comprising a flow-promoting layer interposed between an inner surface of the semipermeable wall and an external surface of at least one of the drug layer and the expandable layer.

3. The dosage form of claim 1, wherein the liquid active agent formulation comprises a self-emulsifying formulation.

4. The dosage form of claim 3, wherein the active agent has low water solubility.

5. The dosage form of claim 1, wherein the liquid active agent formulation comprises an absorption enhnacer.

* * * * *